(12) United States Patent
Brenner

(10) Patent No.: US 8,124,336 B2
(45) Date of Patent: Feb. 28, 2012

(54) METHODS AND COMPOSITIONS FOR REDUCING THE COMPLEXITY OF A NUCLEIC ACID SAMPLE

(75) Inventor: Sydney Brenner, Ely (GB)

(73) Assignee: Population Genetics Technologies Ltd, Cambridge (GB)

( * ) Notice: Subject to any disclaimer, the term of this patent is extended or adjusted under 35 U.S.C. 154(b) by 181 days.

(21) Appl. No.: 12/236,377

(22) Filed: Sep. 23, 2008

(65) Prior Publication Data

US 2009/0081737 A1 Mar. 26, 2009

Related U.S. Application Data

(60) Provisional application No. 60/975,452, filed on Sep. 26, 2007.

(51) Int. Cl.
*C12Q 1/68* (2006.01)
(52) U.S. Cl. ........................................................ 435/6.1
(58) Field of Classification Search ........................ None
See application file for complete search history.

(56) References Cited

U.S. PATENT DOCUMENTS

| | | | |
|---|---|---|---|
| 5,484,701 A | 1/1996 | Cocuzza | |
| 5,635,400 A | 6/1997 | Brenner | |
| 5,695,934 A | 12/1997 | Brenner | |
| 5,714,330 A | 2/1998 | Brenner et al. | |
| 5,728,524 A | 3/1998 | Sibson | |
| 5,763,175 A | 6/1998 | Brenner | |
| 5,846,719 A | 12/1998 | Brenner et al. | |
| 5,876,936 A | 3/1999 | Ju | |
| 6,046,005 A | 4/2000 | Ju et al. | |
| 6,124,092 A | 9/2000 | O'Neill et al. | |
| 6,287,778 B1 | 9/2001 | Huang et al. | |
| 6,287,825 B1 | 9/2001 | Weissman et al. | |
| 6,468,749 B1 | 10/2002 | Ulanovsky et al. | |
| 6,514,699 B1 | 2/2003 | O'Neill et al. | |
| 6,958,225 B2 | 10/2005 | Dong | |
| 7,108,976 B2 * | 9/2006 | Jones et al. | 435/6 |
| 7,217,522 B2 | 5/2007 | Brenner | |
| 2003/0032020 A1 | 2/2003 | Brenner | |
| 2003/0049616 A1 | 3/2003 | Brenner et al. | |
| 2005/0214825 A1 * | 9/2005 | Stuelpnagel | 435/6 |
| 2006/0046251 A1 | 3/2006 | Sampson et al. | |
| 2006/0063158 A1 * | 3/2006 | Dong et al. | 435/6 |

FOREIGN PATENT DOCUMENTS

| | | |
|---|---|---|
| EP | 1645640 | 4/2006 |
| WO | 2006137733 | 12/2006 |

OTHER PUBLICATIONS

Brenner, et al, "In vitro cloning of complex mixtures of DNA on microbeads: Physical separation of differentially expressed cDNAs," Proc. Natl. Acad. Sci., 97: 1665-1670 (2000).

Brenner, et al, "Gene Expression Analysis by Massively Parallel Signature Sequencing (MPSS) on Microbead Arrays", Nature Biotechnology (2000) 18:630-634.

Czarnik, A.W., "Encoding Methods for Combinatorial Chemistry", Current Opinion in Chemical Biology (1997) 1:60-66.

Fan, et al, "Parallel Genotyping of Human SNPs Using Generic High-density Oligonucleotide Tag Arrays", Genome Research (2000) 10:853-860.

Fan, et al, "A Versatile Assay for High-Throughput Gene Expression Profiling on Universal Array Matrices", Genome Research (2004) 14:878-885.

Gerry, et al, "Universal DNA Microarray Method for Multiplex Detection of Low Abundance Point Mutations", J. Mol. Biol. (1999) 292:251-262.

Ju, "DNA sequencing with solid-phase-capturable dideoxynucleotides and energy transfer primers," Anal. Biochem., 309: 35-39 (2002).

Jordan et al, "Genome complexity reduction for SNP genotyping analysis," Proc. Natl. Acad. Sci., 99: 2942-2947 (2002).

Hirschhorn, et al, "SBE-TAGS: An Array-based Method for Efficient Single-Nucleotide Polymorphism Genotyping", Proc. Natl. Acad. Sci. (2000) 97:12164-12169.

Hughes, et al, "Expression Profiling Using Microarrays Fabricated by an Ink-jet Oligonucleotide Synthesizer", Nature Biotechnology (2001) 19:342-347.

Charnock-Jones et al, "Extension of incomplete cDNAs (ESTs) by biotin/streptavidin-mediated walking using the polymerase chain reaction," J. Biotechnology, 35: 205-215 (1994).

Delios et al, "Separation of complementary strands of plasmid DNA using the biotin-avidin system and its application to heteroduplex formation and RNA/DNA hybridizations in electron microscopy," Nucleic Acids Research, 13: 5457-5469 (1985).

Kandpal et al, "Selective enrichment of a large size genomic DNA fragment by affinity capture: an approach for genome mapping," Nucleic Acids Research, 18: 1789-1795f (1990).

Padgett and Sorge, "Creating seamless junctions independent of restriction sites in PCR cloning," Gene, 168: 31-35 (1996).

* cited by examiner

*Primary Examiner* — Kenneth R. Horlick
*Assistant Examiner* — David Thomas
(74) *Attorney, Agent, or Firm* — James S. Keddie; Bozicevic, Field & Francis, LLP

(57) ABSTRACT

Aspects of the present invention are drawn to methods and compositions for sorting nucleic acid molecules into physically separate compartments according to the identity of a nucleotide base or sequence of bases at a specific location, resulting in the production of reduced complexity samples that find use in any number of downstream genetic analyses. Aspects of the methods of the invention include fragmenting a nucleic acid sample, e.g., with a restriction enzyme, ligating an adaptor (or adaptors), and sorting the fragments based on the identity of the nucleotide base(s) positioned adjacent to the fragmentation site (e.g., the restriction enzyme cut site/or recognition site). Each round of sorting produces binned samples having reduced complexity over the parent sample.

19 Claims, 5 Drawing Sheets

METHODS AND COMPOSITIONS FOR REDUCING THE COMPLEXITY OF A NUCLEIC ACID SAMPLE

CROSS REFERENCE TO RELATED APPLICATION

This application claims priority from U.S. Provisional Application Ser. No. 60/975,452 filed on Sep. 26, 2007, the entirety of which is incorporated herein by reference.

BACKGROUND

A major goal in genetics research is to understand how sequence variations in the genome relate to complex traits, particularly susceptibilities for common diseases such as diabetes, cancer, hypertension, and the like, e.g. Collins et al, Nature, 422: 835-847 (2003). The draft sequence of the human genome has provided a highly useful reference for assessing variation, but it is only a first step towards understanding how the estimated 10 million or more common single nucleotide polymorphisms (SNPs), and other polymorphisms, such as inversions, deletions, insertions, and the like, determine or affect states of health and disease. Many powerful analytical approaches have been developed to address this problem, but none appear to have adequate throughput or flexibility for the types of studies required to associate traits practically and reliably with genomic variation, e.g. Syvanen, Nature Reviews Genetics, 2: 930-942 (2001). For example, it would be desirable to carry out trait-association studies in which a large set of genetic markers from populations of affected and unaffected individuals are compared. Such studies depend on the non-random segregation, or linkage disequilibrium, between the genetic markers and genes involved in the trait or disease being studied. Unfortunately, the extent and distribution of linkage disequilibrium between regions of the human genome is not well understood, but it is currently believed that successful trait-association studies in humans would require the measurement of 30-50,000 markers per individual in populations of at least 300-400 affected individuals and an equal number of controls, Kruglyak and Nickerson, Nature Genetics, 27: 234-236 (2001); Lai, Genome Research, 11: 927-929 (2001); Risch and Merikangas, Science, 273: 1516-1517 (1996); Cardon and Bell, Nature Reviews Genetics, 2: 91-99 (2001).

One approach to dealing with such whole-genome studies is to create subsets of genomic DNA having reduced complexity with respect to the genomes being analyzed in order to simplify the analysis, e.g. Lisitsyn et al, Science, 259: 946-951 (1993); Vos et al, Nucleic Acids Research, 23: 4407-4414 (1995); Dong et al., Genome Research, 11: 1418-1424 (2001); Jordan et al, Proc. Natl. Acad. Sci., 99: 2942-2947 (2002); Weissman et al, U.S. Pat. No. 6,506,562; Sibson, U.S. Pat. No. 5,728,524; Degau et al, U.S. Pat. No. 5,858,656. Unfortunately, most of these techniques rely on some form of subtraction, sequence destruction, or direct or indirect size selection to create subsets, which are difficult to implement and reduce sensitivity.

In view of the above, the field of genetic analysis would be advanced by the availability of a method for converting a highly complex population of DNA, such as a genome or mixture of genomes, into subsets having reduced complexity without requiring subtraction, extraction or other sequence destroying steps.

SUMMARY OF THE INVENTION

Described herein are methods and compositions for producing one or more reduced complexity polynucleotide samples from a parent polynucleotide sample. Aspects of the present invention include sorting polynucleotide molecules into physically separate compartments according to the identity of a nucleotide base or sequence of bases at a specific location, resulting in the production of reduced complexity samples that find use in any number of downstream genetic analyses.

In certain embodiments, polynucleotides in a parent sample are fragmented (e.g., using a restriction enzyme) and adaptors are ligated to the ends of each fragment. The adaptor-ligated fragments are sorted into separate compartments based on the identity of the nucleotide bases positioned adjacent to the site of fragmentation (e.g., the restriction enzyme cut site or recognition site). When all four bases are interrogated at each differentiating nucleotide position, each round of sorting produces sorted (or "binned") samples having up to four-fold reductions in complexity over the previous sample.

In certain embodiments, the steps are repeated (apart from the fragmentation and adaptor ligating step) for a second differentiating nucleotide position in the polynucleotide fragment using a second synthesis primer that anneals such that its 3' base is immediately upstream of the second differentiating nucleotide position in each fragment. Multiple successive rounds of the method may be performed using primers indexed for subsequent differentiating nucleotide positions, with each round generating samples that reduce further the complexity from the initial parent sample.

Aspects of the present invention include methods of producing one or more polynucleotide samples having reduced complexity from a parent polynucleotide sample, the method comprising the steps of: (i) fragmenting polynucleotides in a parent polynucleotide sample; (ii) ligating a first oligonucleotide adapter to the polynucleotide fragments; (iii) annealing a first nucleic acid synthesis primer to the oligonucleotide adapter-ligated fragments, wherein the nucleic acid synthesis primer anneals such that its 3' base is immediately upstream of a first differentiating nucleotide position in each fragment; (iv) contacting the synthesis-primer annealed fragments with a differentiating nucleotide mix under nucleic acid synthesis conditions, wherein the differentiating nucleotide mix comprises one or more nucleotide that is differentially incorporated into the synthesis-primer annealed fragments according to the identity of the nucleotide at the first differentiating nucleotide position; and (v) isolating polynucleotide fragments having a nucleotide of predetermined identity at the first differentiating nucleotide position, wherein the fragments are isolated based on the differential incorporation of the one or more nucleotide, thereby producing a polynucleotide sample having reduced complexity from the parent.

In certain embodiments, the parent polynucleotide sample comprises a mixture of polynucleotides from a plurality of subjects.

In certain embodiments, the polynucleotides from the plurality of subjects are each tagged with a unique identity tag.

In certain embodiments, the unique identity tag is present in the first oligonucleotide adaptor.

In certain embodiments, the differentiating nucleotide mix comprises a nucleotide labeled with a first member of a binding pair.

In certain embodiments, the first member of the binding pair is biotin.

In certain embodiments, the isolating step comprises contacting the sample to a second member of the binding pair immobilized on a substrate, removing unbound polynucleotide fragments and eluting bound fragments from the synthesis primer.

In certain embodiments, steps (iii) to (v) are repeated one or more times at a successive differentiating nucleotide position.

In certain embodiments, step (iv) further comprises separating the synthesis primer-annealed sample into two or more distinct wells, each of which contains a distinct differentiating nucleotide mix and whereby in step (v) multiple distinct isolated samples having reduced complexity from the parent sample are produced, wherein the nucleotide of predetermined identity at the first differentiating nucleotide position is different between the multiple distinct isolated samples.

In certain embodiments, the sequence of the polynucleotides in the parent polynucleotide sample is known, wherein the polynucleotide sample of reduced complexity comprises a predetermined set of nucleic acid fragments based on: (i) the known polynucleotide sequence, and (ii) the identity of the base at the first differentiating nucleotide position.

In certain embodiments, steps (iii) to (v) are repeated one or more times at a successive differentiating nucleotide position, thereby producing multiple polynucleotide samples having reduced complexity from the parent polynucleotide sample, and wherein the resulting polynucleotide samples each comprise a predetermined set of polynucleotide fragments based on the known polynucleotide sequence and the identity of the bases in each of the differentiating nucleotide positions.

In certain embodiments, step (ii) further comprises ligating a second oligonucleotide adaptor to the polynucleotide fragments, wherein the first oligonucleotide adapter and the second oligonucleotide adaptor are ligated to opposite ends of the polynucleotide fragments and the second oligonucleotide adaptor comprises a region differing in sequence from the first oligonucleotide adaptor; step (iv) further comprises immobilizing the nucleic acid fragments by hybridization to a capture primer immobilized on a substrate, wherein the capture primer hybridizes to the region in the second oligonucleotide tag on the same strand of the nucleic acid fragments as the synthesis primer at a location that is downstream of the synthesis primer; the differentiating nucleotide mix comprises nucleic acid synthesis terminating nucleotides representing all nucleotides except a predetermined nucleotide; and step (v) further comprises removing the nucleic acid synthesis-terminating nucleotide mix from the immobilized fragments and isolating polynucleotide fragments that have the predetermined nucleotide by contacting the immobilized synthesis-primer annealed fragments with a strand-displacing nucleic acid polymerase under nucleic acid synthesis conditions in the presence of all four nucleotide bases such that fragments that have the predetermined nucleotide at the first differentiating nucleotide position are eluted from the immobilization primer by virtue of the strand-displacing activity of the strand-displacing polymerase.

In certain embodiments, the synthesis primer comprises a capture moiety.

In certain embodiments, the sequence of the polynucleotides in the parent polynucleotide sample is known, wherein the polynucleotide sample of reduced complexity comprises a predetermined set of nucleic acid fragments based on: (i) the known polynucleotide sequence, and (ii) the identity of the base at the first differentiating nucleotide position.

In certain embodiments, steps (iii) to (v) are repeated one or more times at a successive differentiating nucleotide position, thereby producing multiple polynucleotide samples having reduced complexity from the parent polynucleotide sample, and wherein the resulting polynucleotide samples each comprise a predetermined set of polynucleotide fragments based on the known polynucleotide sequence and the identity of the bases in each of the differentiating nucleotide positions.

Aspects of the present invention include obtaining a polynucleotide sample having reduced complexity from a parent polynucleotide sample produced by the methods detailed herein.

In certain embodiments, the polynucleotide sample having reduced complexity is modified prior to the obtaining.

Aspects of the present invention include one or more polynucleotide sample having reduced complexity from a parent polynucleotide sample produced by the methods detailed herein.

BRIEF DESCRIPTION OF THE DRAWINGS

The invention is best understood from the following detailed description when read in conjunction with the accompanying drawings. It is emphasized that, according to common practice, the various features of the drawings are not to-scale. Indeed, the dimensions of the various features are arbitrarily expanded or reduced for clarity. Included in the drawings are the following figures.

DEFINITIONS

Figure 1:
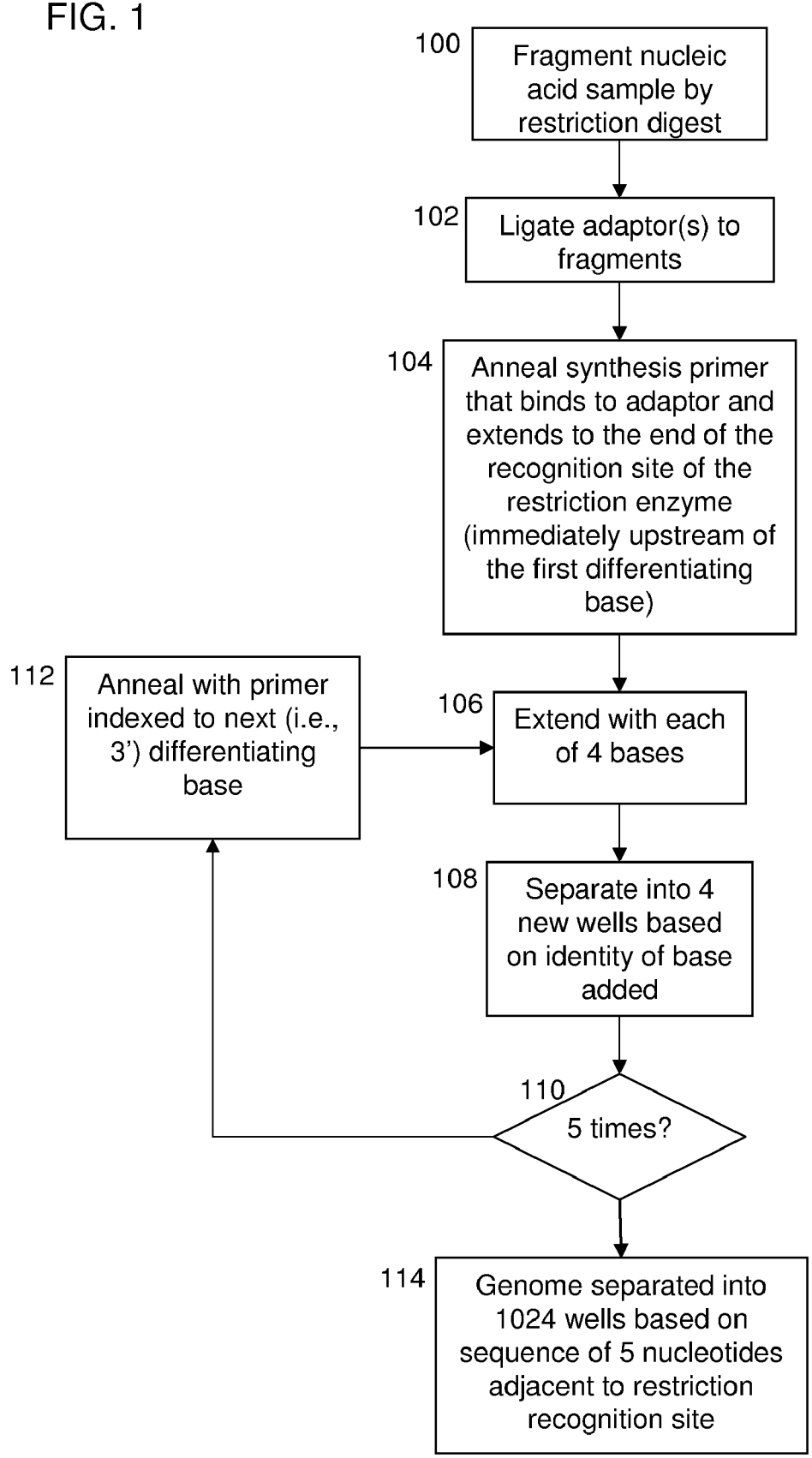
FIG. 1 provides a flow chart of an exemplary embodiment of the sorting methods of the present invention.

Unless otherwise defined, all technical and scientific terms used herein have the same meaning as commonly understood by one of ordinary skill in the art to which this invention belongs. Still, certain elements are defined for the sake of clarity and ease of reference.

Terms and symbols of nucleic acid chemistry, biochemistry, genetics, and molecular biology used herein follow those of standard treatises and texts in the field, e.g. Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); and the like.

"Addressable" in reference to tag complements means that the nucleotide sequence, or perhaps other physical or chemical characteristics, of an end-attached probe, such as a tag complement, can be determined from its address, i.e. a one-to-one correspondence between the sequence or other property of the end-attached probe and a spatial location on, or characteristic of, the solid phase support to which it is attached. Preferably, an address of a tag complement is a spatial location, e.g. the planar coordinates of a particular region containing copies of the end-attached probe. However, end-attached probes may be addressed in other ways too, e.g. by microparticle size, shape, color, frequency of micro-transponder, or the like, e.g. Chandler et al, PCT publication WO 97/14028.

"Amplicon" means the product of a polynucleotide amplification reaction. That is, it is a population of polynucleotides, usually double stranded, that are replicated from one or more starting sequences. The one or more starting sequences may be one or more copies of the same sequence, or it may be a mixture of different sequences. Amplicons may be produced by a variety of amplification reactions whose products are multiple replicates of one or more target nucleic acids. Generally, amplification reactions producing amplicons are "template-driven" in that base pairing of reactants, either nucleotides or oligonucleotides, have complements in a template polynucleotide that are required for the creation of reaction products. In one aspect, template-driven reactions are primer extensions with a nucleic acid polymerase or oligonucleotide ligations with a nucleic acid ligase. Such reactions include, but are not limited to, polymerase chain reactions (PCRs), linear polymerase reactions, nucleic acid sequence-based amplification (NASBAs), rolling circle amplifications, and the like, disclosed in the following references that are incorporated herein by reference: Mullis et al, U.S. Pat. Nos. 4,683,195; 4,965,188; 4,683,202; 4,800,159 (PCR); Gelfand et al, U.S. Pat. No. 5,210,015 (real-time PCR with "TAQMAN®" probes); Wittwer et al, U.S. Pat. No. 6,174,670; Kacian et al, U.S. Pat. No. 5,399,491 ("NASBA"); Lizardi, U.S. Pat. No. 5,854,033; Aono et al, Japanese patent publ. JP 4-262799 (rolling circle amplification); and the like. In one aspect, amplicons of the invention are produced by PCRs. An amplification reaction may be a "real-time" amplification if a detection chemistry is available that permits a reaction product to be measured as the amplification reaction progresses, e.g. "real-time PCR" described below, or "real-time NASBA" as described in Leone et al, Nucleic Acids Research, 26: 2150-2155 (1998), and like references. As used herein, the term "amplifying" means performing an amplification reaction. A "reaction mixture" means a solution containing all the necessary reactants for performing a reaction, which may include, but not be limited to, buffering agents to maintain pH at a selected level during a reaction, salts, co-factors, scavengers, and the like.

The term "assessing" includes any form of measurement, and includes determining if an element is present or not. The terms "determining", "measuring", "evaluating", "assessing" and "assaying" are used interchangeably and includes quantitative and qualitative determinations. Assessing may be relative or absolute. "Assessing the presence of" includes determining the amount of something present, and/or determining whether it is present or absent. As used herein, the terms "determining," "measuring," and "assessing," and "assaying" are used interchangeably and include both quantitative and qualitative determinations.

"Complementary or substantially complementary" refers to the hybridization or base pairing or the formation of a duplex between nucleotides or nucleic acids, such as, for instance, between the two strands of a double stranded DNA molecule or between an oligonucleotide primer and a primer binding site on a single stranded nucleic acid. Complementary nucleotides are, generally, A and T (or A and U), or C and G. Two single stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, M. Kanehisa Nucleic Acids Res. 12:203 (1984), incorporated herein by reference.

"Duplex" means at least two oligonucleotides and/or polynucleotides that are fully or partially complementary undergo Watson-Crick type base pairing among all or most of their nucleotides so that a stable complex is formed. The terms "annealing" and "hybridization" are used interchangeably to mean the formation of a stable duplex. "Perfectly matched" in reference to a duplex means that the poly- or oligonucleotide strands making up the duplex form a double stranded structure with one another such that every nucleotide in each strand undergoes Watson-Crick basepairing with a nucleotide in the other strand. The term "duplex" comprehends the pairing of nucleoside analogs, such as deoxyinosine, nucleosides with 2-aminopurine bases, PNAs, LNA's and the like, that may be employed. A "mismatch" in a duplex between two oligonucleotides or polynucleotides means that one or more nucleotides in the duplex fails to undergo Watson-Crick bonding.

"Genetic locus," "locus," or "locus of interest" in reference to a genome or target polynucleotide, means a contiguous sub-region or segment of the genome or target polynucleotide. As used herein, genetic locus, locus, or locus of interest may refer to the position of a nucleotide, a gene or a portion of a gene in a genome, including mitochondrial DNA or other non-chromosomal DNA (e.g., bacterial plasmid), or it may refer to any contiguous portion of genomic sequence whether or not it is within, or associated with, a gene. A genetic locus, locus, or locus of interest can be from a single nucleotide to a segment of a few hundred or a few thousand nucleotides in length or more. In general, a locus of interest will have a reference sequence associated with it (see description of "reference sequence" below).

"Genetic variant" means a substitution, inversion, insertion, or deletion of one or more nucleotides at genetic locus, or a translocation of DNA from one genetic locus to another genetic locus. In one aspect, genetic variant means an alternative nucleotide sequence at a genetic locus that may be present in a population of individuals and that includes nucleotide substitutions, insertions, and deletions with respect to other members of the population. In another aspect, genetic variants include amplifications, translocations, insertions, deletions, and other alterations of entire sections of a genome, e.g., as observed in comparative genome hybridization analyses (CGH).

"Kit" refers to any delivery system for delivering materials or reagents for carrying out a method of the invention. In the context of reaction assays, such delivery systems include systems that allow for the storage, transport, or delivery of reaction reagents (e.g., probes, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. Such contents may be delivered to the intended recipient together or separately. For example, a first container may contain an enzyme for use in an assay, while a second container contains probes.

"Ligation" means to form a covalent bond or linkage between the termini of two or more nucleic acids, e.g. oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon of a terminal nucleotide of one oligonucleotide with 3' carbon of another oligonucleotide. A variety of template-driven ligation reactions are described in the following references, which are incorporated by reference: Whiteley et al, U.S. Pat. No. 4,883,750; Letsinger et al, U.S. Pat. No. 5,476,930; Fung et al, U.S. Pat. No. 5,593,826; Kool, U.S. Pat. No. 5,426,180; Landegren et al, U.S. Pat. No. 5,871,921; Xu and Kool, Nucleic Acids Research, 27: 875-881 (1999); Higgins et al, Methods in Enzymology, 68: 50-71 (1979); Engler et al, The Enzymes, 15: 3-29 (1982); and Namsaraev, U.S. patent publication 2004/0110213.

"Microarray" refers to a solid phase support having a planar surface, which carries an array of nucleic acids, each member of the array comprising identical copies of an oligonucleotide or polynucleotide immobilized to a spatially defined region or site, which does not overlap with those of other members of the array; that is, the regions or sites are spatially discrete. Spatially defined hybridization sites may additionally be "addressable" in that its location and the identity of its immobilized oligonucleotide are known or predetermined, for example, prior to its use. Typically, the oligonucleotides or polynucleotides are single stranded and are covalently attached to the solid phase support, usually by a 5'-end or a 3'-end. The density of non-overlapping regions containing nucleic acids in a microarray is typically greater than 100 per $cm^2$, and more preferably, greater than 1000 per $cm^2$. Microarray technology is reviewed in the following references: Schena, Editor, Microarrays: A Practical Approach (IRL Press, Oxford, 2000); Southern, Current Opin. Chem. Biol., 2: 404-410 (1998); Nature Genetics Supplement, 21: 1-60 (1999). As used herein, "random microarray" refers to a microarray whose spatially discrete regions of oligonucleotides or polynucleotides are not spatially addressed. That is, the identity of the attached oligonucleotides or polynucleotides is not discernable, at least initially, from its location. In one aspect, random microarrays are planar arrays of microbeads wherein each microbead has attached a single kind of hybridization tag complement, such as from a minimally cross-hybridizing set of oligonucleotides. Arrays of microbeads may be formed in a variety of ways, e.g. Brenner et al, Nature Biotechnology, 18: 630-634 (2000); Tulley et al, U.S. Pat. No. 6,133,043; Stuelpnagel et al, U.S. Pat. No. 6,396,995; Chee et al, U.S. Pat. No. 6,544,732; and the like. Likewise, after formation, microbeads, or oligonucleotides thereof, in a random array may be identified in a variety of ways, including by optical labels, e.g. fluorescent dye ratios or quantum dots, shape, sequence analysis, or the like.

"Modified" when used to describe a reduced complexity sample according to the subject invention shall mean that the reduced complexity sample has been altered (e.g., chemically, enzymatically, physically, etc.), processed or analyzed further. For example, a modified reduced complexity sample can be processed in such a manner so as to isolate from the sample certain regions of the genome or transcriptome and/or has been processed in such a manner as that enables sequences different from a reference or wild-type to be isolated from a mixture of genomic or transcriptomic samples (see, for example, U.S. patent application Ser. No. 11/656,746, incorporated herein by reference in its entirety). Additionally, a modified reduced complexity sample may be produced by combining two or more reduced complexity samples (or previously-modified reduced complexity samples). In certain embodiments, modified reduced complexity samples find use in facilitating further downstream analyses, e.g., sequencing.

"Nucleoside" as used herein includes the natural nucleosides, including 2'-deoxy and 2'-hydroxyl forms, e.g. as described in Kornberg and Baker, DNA Replication, 2nd Ed.

(Freeman, San Francisco, 1992). "Analogs" in reference to nucleosides includes synthetic nucleosides having modified base moieties and/or modified sugar moieties, e.g. described by Scheit, Nucleotide Analogs (John Wiley, New York, 1980); Uhlman and Peyman, Chemical Reviews, 90: 543-584 (1990), or the like, with the proviso that they are capable of specific hybridization. Such analogs include synthetic nucleosides designed to enhance binding properties, reduce complexity, increase specificity, and the like. Polynucleotides comprising analogs with enhanced hybridization or nuclease resistance properties are described in Uhlman and Peyman (cited above); Crooke et al, Exp. Opin. Ther. Patents, 6: 855-870 (1996); Mesmaeker et al, Current Opinion in Structual Biology, 5: 343-355 (1995); and the like. Exemplary types of polynucleotides that are capable of enhancing duplex stability include oligonucleotide N3+→P5' phosphoramidates (referred to herein as "amidates"), peptide nucleic acids (referred to herein as "PNAs"), oligo-2'-O-alkylribonucleotides, polynucleotides containing C-5 propynylpyrimidines, locked nucleic acids ("LNAs"), and like compounds. Such oligonucleotides are either available commercially or may be synthesized using methods described in the literature.

"Polymerase chain reaction," or "PCR," means a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g. exemplified by the references: McPherson et al, editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature >90° C., primers annealed at a temperature in the range 50-75° C., and primers extended at a temperature in the range 72-78° C. The term "PCR" encompasses derivative forms of the reaction, including but not limited to, RT-PCR, real-time PCR, nested PCR, quantitative PCR, multiplexed PCR, and the like. Reaction volumes range from a few hundred nanoliters, e.g. 200 nL, to a few hundred μL, e.g. 200 μL. "Reverse transcription PCR," or "RT-PCR," means a PCR that is preceded by a reverse transcription reaction that converts a target RNA to a complementary single stranded DNA, which is then amplified, e.g. Tecott et al, U.S. Pat. No. 5,168,038, which patent is incorporated herein by reference. "Real-time PCR" means a PCR for which the amount of reaction product, i.e. amplicon, is monitored as the reaction proceeds. There are many forms of real-time PCR that differ mainly in the detection chemistries used for monitoring the reaction product, e.g. Gelfand et al, U.S. Pat. No. 5,210,015 ("TAQMAN®"); Wittwer et al, U.S. Pat. Nos. 6,174,670 and 6,569,627 (intercalating dyes); Tyagi et al, U.S. Pat. No. 5,925,517 (molecular beacons); which patents are incorporated herein by reference. Detection chemistries for real-time PCR are reviewed in Mackay et al, Nucleic Acids Research, 30: 1292-1305 (2002), which is also incorporated herein by reference. "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al, Anal. Biochem., 273: 221-228 (1999) (two-color real-time PCR). Usually, distinct sets of primers are employed for each sequence being amplified.

"Quantitative PCR" means a PCR designed to measure the abundance of one or more specific target sequences in a sample or specimen. Quantitative PCR includes both absolute quantitation and relative quantitation of such target sequences. Quantitative measurements are made using one or more reference sequences that may be assayed separately or together with a target sequence. The reference sequence may be endogenous or exogenous to a sample or specimen, and in the latter case, may comprise one or more competitor templates. Typical endogenous reference sequences include segments of transcripts of the following genes: β-actin, GAPDH, $β_2$-microglobulin, ribosomal RNA, and the like. Techniques for quantitative PCR are well-known to those of ordinary skill in the art, as exemplified in the following references that are incorporated by reference: Freeman et al, Biotechniques, 26: 112-126 (1999); Becker-Andre et al, Nucleic Acids Research, 17: 9437-9447 (1989); Zimmerman et al, Biotechniques, 21: 268-279 (1996); Diviacco et al, Gene, 122: 3013-3020 (1992); Becker-Andre et al, Nucleic Acids Research, 17: 9437-9446 (1989); and the like.

"Polynucleotide" or "oligonucleotide" are used interchangeably and each mean a linear polymer of nucleotide monomers. Monomers making up polynucleotides and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like. Such monomers and their internucleosidic linkages may be naturally occurring or may be analogs thereof, e.g. naturally occurring or non-naturally occurring analogs. Non-naturally occurring analogs may include PNAs, LNAs, phosphorothioate internucleosidic linkages, bases containing linking groups permitting the attachment of labels, such as fluorophores, or haptens, and the like. Whenever the use of an oligonucleotide or polynucleotide requires enzymatic processing, such as extension by a polymerase, ligation by a ligase, or the like, one of ordinary skill would understand that oligonucleotides or polynucleotides in those instances would not contain certain analogs of internucleosidic linkages, sugar moieties, or bases at any or some positions. Polynucleotides typically range in size from a few monomeric units, e.g. 5-40, when they are usually referred to as "oligonucleotides," to several thousand monomeric units. Whenever a polynucleotide or oligonucleotide is represented by a sequence of letters (upper or lower case), such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, Human Molecular Genetics 2 (Wiley-Liss, New York, 1999). Usually polynucleotides comprise the four natural nucleosides (e.g. deoxyadenosine, deoxycytidine, deoxyguanosine, deoxythymidine for DNA or their ribose counterparts for RNA) linked by phosphodiester linkages; however, they may also comprise non-natural nucleotide analogs, e.g. including modified bases, sugars, or internucleosidic linkages. It is clear to those skilled in the art that where an enzyme has specific oligonucleotide or polynucleotide substrate requirements for activity, e.g. single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al, Molecular Cloning, Second Edition (Cold Spring Harbor Laboratory, New York, 1989), and like references.

"Primer" means an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Usually primers are extended by a DNA polymerase. Primers are generally of a length compatible with its use in synthesis of primer extension products, and are usually are in the range of between 8 to 100 nucleotides in length, such as 10 to 75, 15 to 60, 15 to 40, 18 to 30, 20 to 40, 21 to 50, 22 to 45, 25 to 40, and so on, more typically in the range of between 18-40, 20-35, 21-30 nucleotides long, and any length between the stated ranges. Typical primers can be in the range of between 10-50 nucleotides long, such as 15-45, 18-40, 20-30, 21-25 and so on, and any length between the stated ranges. In some embodiments, the primers are usually not more than about 10, 12, 15, 20, 21, 22, 23, 24, 25, 26, 27, 28, 29, 30, 35, 40, 45, 50, 55, 60, 65, or 70 nucleotides in length.

Primers are usually single-stranded for maximum efficiency in amplification, but may alternatively be double-stranded. If double-stranded, the primer is usually first treated to separate its strands before being used to prepare extension products. This denaturation step is typically effected by heat, but may alternatively be carried out using alkali, followed by neutralization. Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

A "primer pair" as used herein refers to first and second primers having nucleic acid sequence suitable for nucleic acid-based amplification of a target nucleic acid. Such primer pairs generally include a first primer having a sequence that is the same or similar to that of a first portion of a target nucleic acid, and a second primer having a sequence that is complementary to a second portion of a target nucleic acid to provide for amplification of the target nucleic acid or a fragment thereof. Reference to "first" and "second" primers herein is arbitrary, unless specifically indicated otherwise. For example, the first primer can be designed as a "forward primer" (which initiates nucleic acid synthesis from a 5' end of the target nucleic acid) or as a "reverse primer" (which initiates nucleic acid synthesis from a 5' end of the extension product produced from synthesis initiated from the forward primer). Likewise, the second primer can be designed as a forward primer or a reverse primer.

"Readout" means a parameter, or parameters, which are measured and/or detected that can be converted to a number or value. In some contexts, readout may refer to an actual numerical representation of such collected or recorded data. For example, a readout of fluorescent intensity signals from a microarray is the address and fluorescence intensity of a signal being generated at each hybridization site of the microarray; thus, such a readout may be registered or stored in various ways, for example, as an image of the microarray, as a table of numbers, or the like.

"Solid support", "support", and "solid phase support" are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. Microarrays usually comprise at least one planar solid phase support, such as a glass microscope slide.

"Specific" or "specificity" in reference to the binding of one molecule to another molecule, such as a labeled target sequence for a probe, means the recognition, contact, and formation of a stable complex between the two molecules, together with substantially less recognition, contact, or complex formation of that molecule with other molecules. In one aspect, "specific" in reference to the binding of a first molecule to a second molecule means that to the extent the first molecule recognizes and forms a complex with another molecule in a reaction or sample, it forms the largest number of the complexes with the second molecule. Preferably, this largest number is at least fifty percent. Generally, molecules involved in a specific binding event have areas on their surfaces or in cavities giving rise to specific recognition between the molecules binding to each other. Examples of specific binding include antibody-antigen interactions, enzyme-substrate interactions, formation of duplexes or triplexes among polynucleotides and/or oligonucleotides, receptor-ligand interactions, and the like. As used herein, "contact" in reference to specificity or specific binding means two molecules are close enough that weak noncovalent chemical interactions, such as Van der Waal forces, hydrogen bonding, base-stacking interactions, ionic and hydrophobic interactions, and the like, dominate the interaction of the molecules.

As used herein, the term "$T_m$" is used in reference to the "melting temperature." The melting temperature is the temperature (as measured in ° C.) at which a population of double-stranded nucleic acid molecules becomes half dissociated into single strands. Several equations for calculating the Tm of nucleic acids are well known in the art. As indicated by standard references, a simple estimate of the Tm value in degrees Celsius may be calculated by the equation. Tm=81.5+0.41 (% G+C), when a nucleic acid is in aqueous solution at 1 M NaCl (see e.g., Anderson and Young, Quantitative Filter Hybridization, in Nucleic Acid Hybridization (1985). Other references (e.g., Allawi, H. T. & SantaLucia, J., Jr., Biochemistry 36, 10581-94 (1997)) include alternative methods of computation which take structural and environmental, as well as sequence characteristics into account for the calculation of Tm.

The terms "upstream" and "downstream" in describing nucleic acid molecule orientation and/or polymerization are used herein as understood by one of skill in the art. As such, "downstream" generally means proceeding in the 5' to 3' direction, i.e., the direction in which a nucleotide polymerase normally extends a sequence, and "upstream" generally means the converse. For example, a first primer that hybridizes "upstream" of a second primer on the same target nucleic acid molecule is located on the 5' side of the second primer (and thus nucleic acid polymerization from the first primer proceeds towards the second primer).

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

DETAILED DESCRIPTION OF THE INVENTION

The invention provides methods and compositions for sorting polynucleotides based on sequence characteristics to form subpopulations of reduced complexity (as compared to the parent sample). Reduced complexity samples produced by the methods described herein are also provided. In certain aspects, such sorting methods are used reduce the complexity of a polynucleotide sample derived from a single subject (or source, e.g., a human), whereas in other aspects, the sorting methods are used to reduce the complexity of polynucleotide samples containing a mixture of polynucleotides from a plurality of subjects (e.g., genomic DNA fragments from multiple sources, e.g., human subjects). In certain embodiments, the polynucleotides from the plurality of subjects are each tagged with a unique identity tag which serves to allow the subject from which each polynucleotide was derived to be determined, e.g., after further sample manipulation/analysis. Determining the identity of the identity tag associated with a polynucleotide can be accomplished by any convenient method, e.g. sequencing assays, differential hybridization assays, etc. Moreover, by reducing complexity of samples in a sequence specific manner (according to the identity of bases in the fragments that are present at specific differentiating nucleotide positions), aspects of the present invention greatly facilitate analysis of sequence characteristics of the fragments themselves, e.g., by sequencing, differential hybridization, or any other assay for analyzing sequence characteristics of a fragment of interest. In certain embodiments, both the identity of the subject from which a fragment is derived and a sequence characteristic of the fragment itself is determined.

In one aspect, a sorting method of the invention is carried out by the following steps: (i) fragmenting polynucleotides in a parent polynucleotide sample; (ii) ligating an oligonucleotide adapter to the polynucleotide fragments; (iii) annealing a first nucleic acid synthesis primer to the oligonucleotide adapter-ligated fragments, where the nucleic acid synthesis primer anneals such that its 3' base is immediately upstream of a first differentiating nucleotide position in each fragment; (iv) contacting the synthesis-primer annealed fragments with a differentiating nucleotide mix under nucleic acid synthesis conditions, wherein said differentiating nucleotide mix comprises one or more nucleotide that is differentially incorporated into the synthesis-primer annealed fragments according to the identity of the nucleotide at the first differentiating nucleotide position; and (v) isolating polynucleotide fragments having a nucleotide of predetermined identity at the first differentiating nucleotide position, wherein the fragments are isolated based on the differential incorporation of the one or more nucleotide, thereby producing a polynucleotide sample having reduced complexity from the parent.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as Genome Analysis: A Laboratory Manual Series (Vols. I-IV), *Using Antibodies: A Laboratory Manual, Cells: A Laboratory Manual, PCR Primer: A Laboratory Manual, and Molecular Cloning: A Laboratory Manual* (all from Cold Spring Harbor Laboratory Press), Stryer, L. (1995) *Biochemistry* (4th Ed.) Freeman, New York, Gait, *"Oligonucleotide Synthesis: A Practical Approach"* 1984, IRL Press, London, Nelson and Cox (2000), Lehninger, A., *Principles of Biochemistry* $3^{rd}$ Ed., W. H. Freeman Pub., New York, N.Y. and Berg et al. (2002) *Biochemistry,* $5^{th}$ Ed., W. H. Freeman Pub., New York, N.Y., all of which are herein incorporated in their entirety by reference for all purposes.

As summarized above, aspects of the present invention are drawn to methods and compositions for sorting polynucleotide fragments (e.g., DNA molecules) into physically separate compartments according to the identity of a nucleotide base or sequence of bases at a specific location, resulting in the production of reduced complexity samples that find use in any number of downstream genetic analyses.

An exemplary flow chart of a complexity-reducing method according to aspects of the invention is shown in FIG. 1 for the specific example of a complexity reduction based on the 5 nucleotides adjacent to the adaptor. At step 100, a nucleic acid sample is fragmented in a sequence-specific manner (e.g., by restriction enzyme digestion). At step 102, an oligonucleotide adaptor is ligated to the end of the fragments. In certain embodiments, the adaptor relevant to the sorting process is ligated to only one end of the fragments while in certain other embodiments adaptors are ligated to both ends of the fragments. In these latter embodiments, the adaptor ligated to the first and second of the fragment are the same whereas in other embodiments the adaptor at one end is different from the adaptor at the other end. For example, a first adaptor may include all or part of a synthesis primer binding site (as described below) while the second adaptor may be used as a unique tag or a binding domain to attach the fragment to a solid support (e.g., by hybridizing it to a substrate-immobilized complementary oligonucleotide). In certain embodiments, an adaptor may serve as both a primer binding site and a unique tag.

At step 104, a synthesis primer is annealed that binds to the ligated adaptor and extends to immediately upstream (i.e., with regard to the direction of nucleic acid synthesis) of the first differentiating nucleotide position (or sorting nucleotide position) in the adaptor-ligated fragment. By "first differentiating nucleotide position" is meant the first nucleotide position in the fragment (starting from the end of the adaptor ligated fragment) whose identity is not already known (i.e., because the nucleic acid sample is a mixture of different fragments having different sequences). As such, the first differentiating nucleotide position can be used, according to aspects of the present invention, to differentiate the fragments in the sample form each other and sort them accordingly (as described below). In certain embodiments, the synthesis primer extends to the end of the recognition site of the restriction enzyme used to fragment the nucleic acid sample (e.g., for Type II restriction enzymes which cut within the recognition site for the enzyme). For example, if the nucleic acid sample was cut with EcoRI (5' G/AATTC 3') and ligated with an adaptor having an EcoRI-compatible end, the 3' end of the synthesis primer would end with the sequence GAATTC (in the 5' to 3' direction). In certain other embodiments, the synthesis primer extends to the end of the adaptor sequence ligated to the fragments. For example, if the nucleic acid sample was cut with the Type IIs restriction enzyme Bcc I (5' CCATC (4/5) 3'), the 5' overhang filled in (blunted), and the adaptor ligated to the blunt end, then the 3' end of the synthesis primer would end at the 3' end of the adaptor sequence.

At steps 106 and 108, the annealed fragments are extended (placed under nucleic acid synthesis conditions) in the presence of a differentiating nucleotide mix which includes the four different nucleotide bases (A, G, C, and T) so as to allow isolation of fragments having a predetermined nucleotide at the first differentiating nucleotide position. Following the extension step, the fragments are separated into four samples based on the identity of the base added. In certain embodiments, the separation is achieved by virtue of a capture moiety attached to each base in the differentiating nucleotide mix, where the desired fragments can be isolated by contacting the extended samples to a substrate-bound binding partner for the capture moiety. In certain embodiments, the extensions are done in four separate reactions (i.e., splitting the sample into four parts), with each sample having a distinct differentiating nucleotide mix. In these embodiments, the same capture moiety can be use for each base (e.g., the bases are biotinylated). In certain embodiments, each base in the differentiating nucleotide mix has a distinct capture moiety such that fragments having a particular base added can be captured using a substrate-bound binding partner specific for the corresponding capture moiety on the base.

Figure 3:
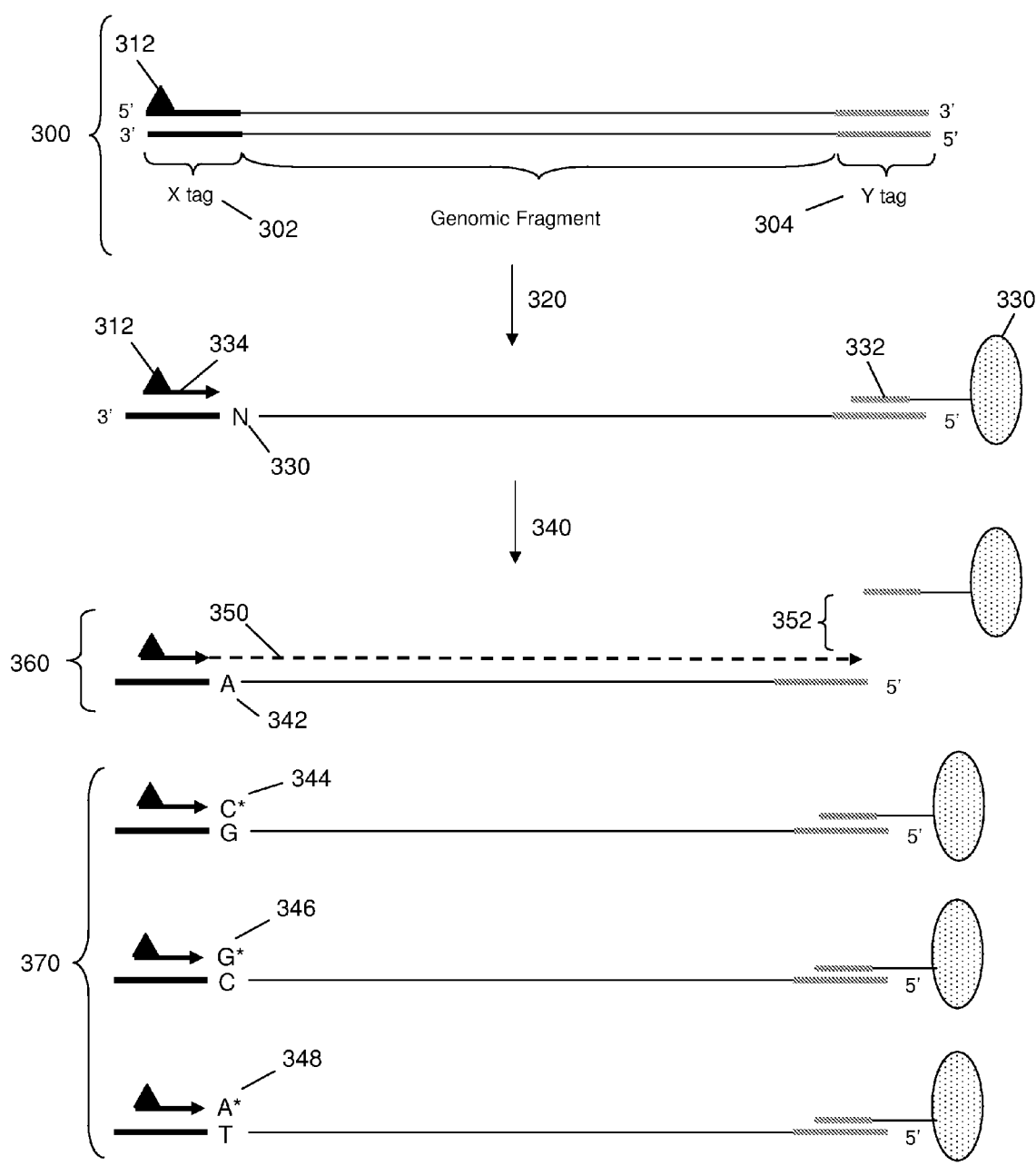
FIG. 3 is a cartoon showing certain aspects of another embodiment of the sorting methods of the present invention.

It is noted here that separating the fragments based on the identity of the nucleotide at a differentiating nucleotide position does not require the use of capture-moiety labeled nucleotide bases. For example, an alternative to such embodiments is discussed below and is shown in FIG. 3.

After the first round of extension and separation, the initial sample has been separated into four samples, each representing fragments having a specific base at the first differentiating nucleotide position.

If additional reduction in complexity is desired, the process can be repeated for the next differentiating nucleotide position. This is illustrated in FIG. 1 in decision box 110 and step 112, in which the process is scheduled to perform 5 rounds of extension and separation. As depicted in step 112, each successive round of extension and separation is designed to interrogate the next differentiating nucleotide position in each fragment (i.e., the nucleotide that is immediately 3' to the previous differentiating nucleotide position). This is achieved by using a synthesis primer that is indexed to the next differentiating nucleotide position as informed by the identity of the nucleotide at the previous differentiating nucleotide position. For example, fragments that have incorporated an "A" in the first round may be hybridized to a synthesis primer identical to the first synthesis primer with the addition of a 3' "A". This will place the next differentiating nucleotide position in the fragment immediately 3' of the synthesis primer.

It is noted here that in certain embodiments, any differentiating nucleotide position can be interrogated for the presence of fewer than all possible bases. For example, an extension reaction for a specific differentiating nucleotide position may include a differentiating nucleotide mix having only a single base such that only fragments that incorporate the single base are isolated (or sorted). Similarly, an extension reaction for a specific differentiating nucleotide position may include a differentiating nucleotide mix (or mixes) having two or three nucleotide bases (either in separate reactions or in a single reaction, as described above) such that only fragments that incorporate one of the two or three bases are isolated into their respective sorted samples.

In certain other embodiments, a user may wish to sort fragments into a single sample that include one of two (or more) specific bases at a differentiating nucleotide position. For example, a user may wish to sort fragments into two samples, the first sample containing fragments that have an A or T at a specific differentiating nucleotide position and a second sample containing fragments that have G or C at a specific differentiating nucleotide position. One way of achieving this is to include two (or more) bases in an extension reaction that are labeled with a common capture moiety. Sorting of fragments using the binding partner of the capture moiety would thus sort fragments into a single sample that include any one of the incorporated bases.

As is clear from above, the specific base or bases interrogated at each differentiating nucleotide position will depend on the desires of the user, and thus can be configured in virtually any way deemed useful in producing reduced complexity samples.

As shown in step 114, once 5 rounds of the process have been completed (i.e., 5 consecutive differentiation bases have been interrogated and sorted), the initial sample has been separated into 1024 different wells, each of which is 512-fold less complex than the initial parent sample (the complexity is only 512-fold less than the parent because a specific fragment will be sorted into a first sample based on the identity of the sequence of the differentiating nucleotide positions interrogated at the first end as well as a second sample based on the identity of the sequence of the differentiating nucleotide positions interrogated at the second end). Each of the fragments present in a well will possess a known 5-base sequence adjacent to the restriction enzyme recognition site (or adjacent to the restriction enzyme cut site, as is the case for Type IIs restriction enzymes as discussed above). This is equivalent to reducing a sample having the complexity of the human genome to 1024 sub-samples each of which has a complexity roughly equivalent to that of a single *E. coli* genome.

It is noted here that the number of steps carried out in the complexity-reducing methods of the present invention can vary widely depending on the desired outcome. As a general rule, the reduction of complexity for each round of the above-described method is four-fold. As such, the fold-reduction of complexity may be estimated as $4^X$, where X is the number of rounds completed (i.e., the number of differentiating nucleotide positions interrogated). However, it is noted here that in certain embodiments, the fold-reduction in complexity may vary at a given step. For example, it is possible to sort based on the presence of more than one base at a given differentiating nucleotide position (as indicated above). In a specific example, one may wish to sort a population according to the presence of A or T versus G or C at a specific differentiating nucleotide position, which would result in a 2-fold reduction in complexity at each step rather than a four-fold reduction as described above. In certain other embodiments, one may wish to sort based on the presence of a specific base at a differentiating nucleotide position (or sequence of differentiating nucleotide positions) to the exclusion of others. In other words, one may not sort and bin all of the nucleic acid fragments present in a sample, but rather sort and bin only a desired subset of fragments while discarding others.

As is evident from the description above, there are numerous ways in which to implement the subject methods which will be dictated largely by the desires of the user and/or the specifics of the downstream genetic assays that will be conducted using the sorted fragments.

Figure 2:
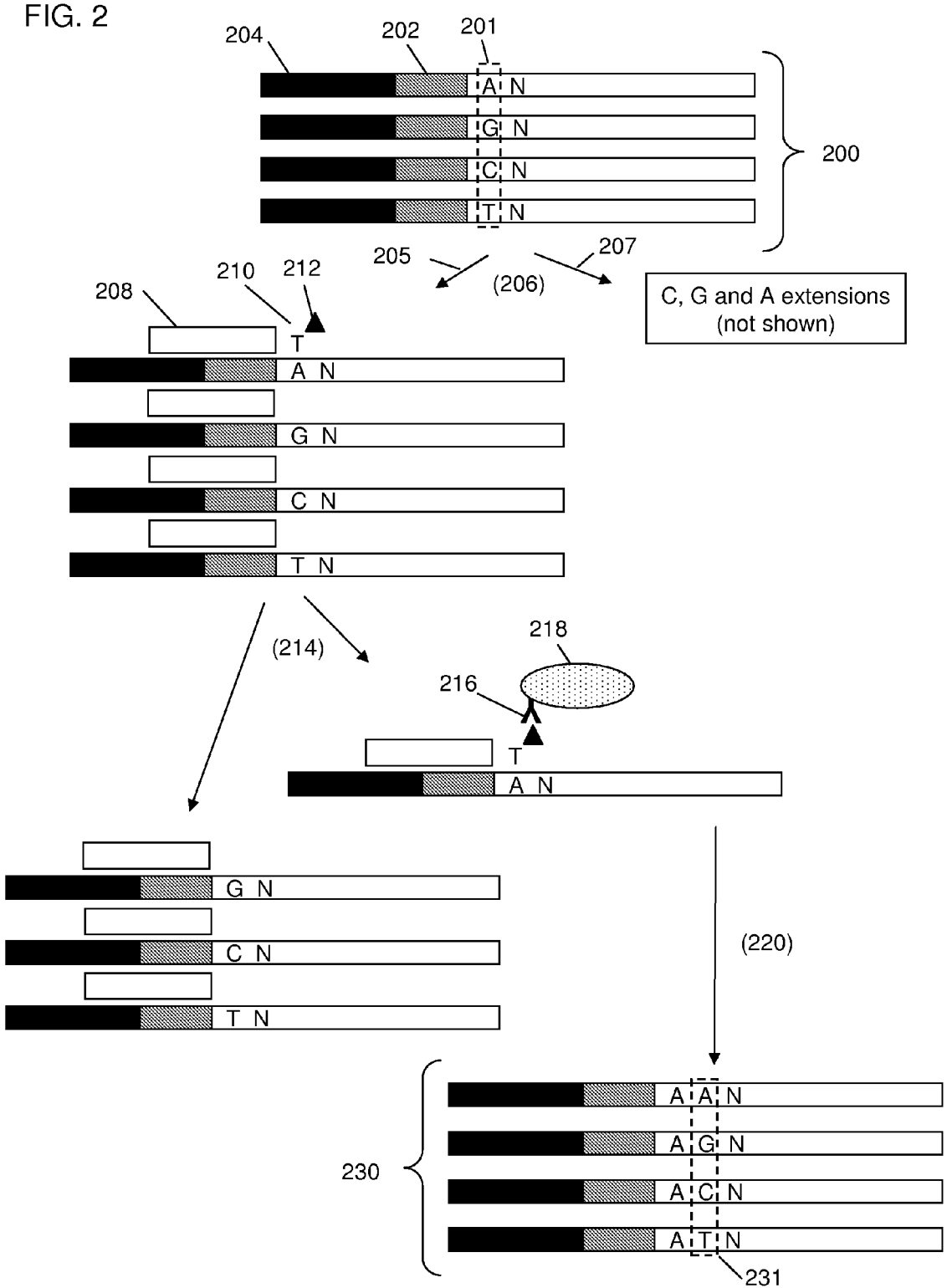
FIG. 2 is a cartoon showing certain aspects of one embodiment of the sorting methods of the present invention.
Figure 2:
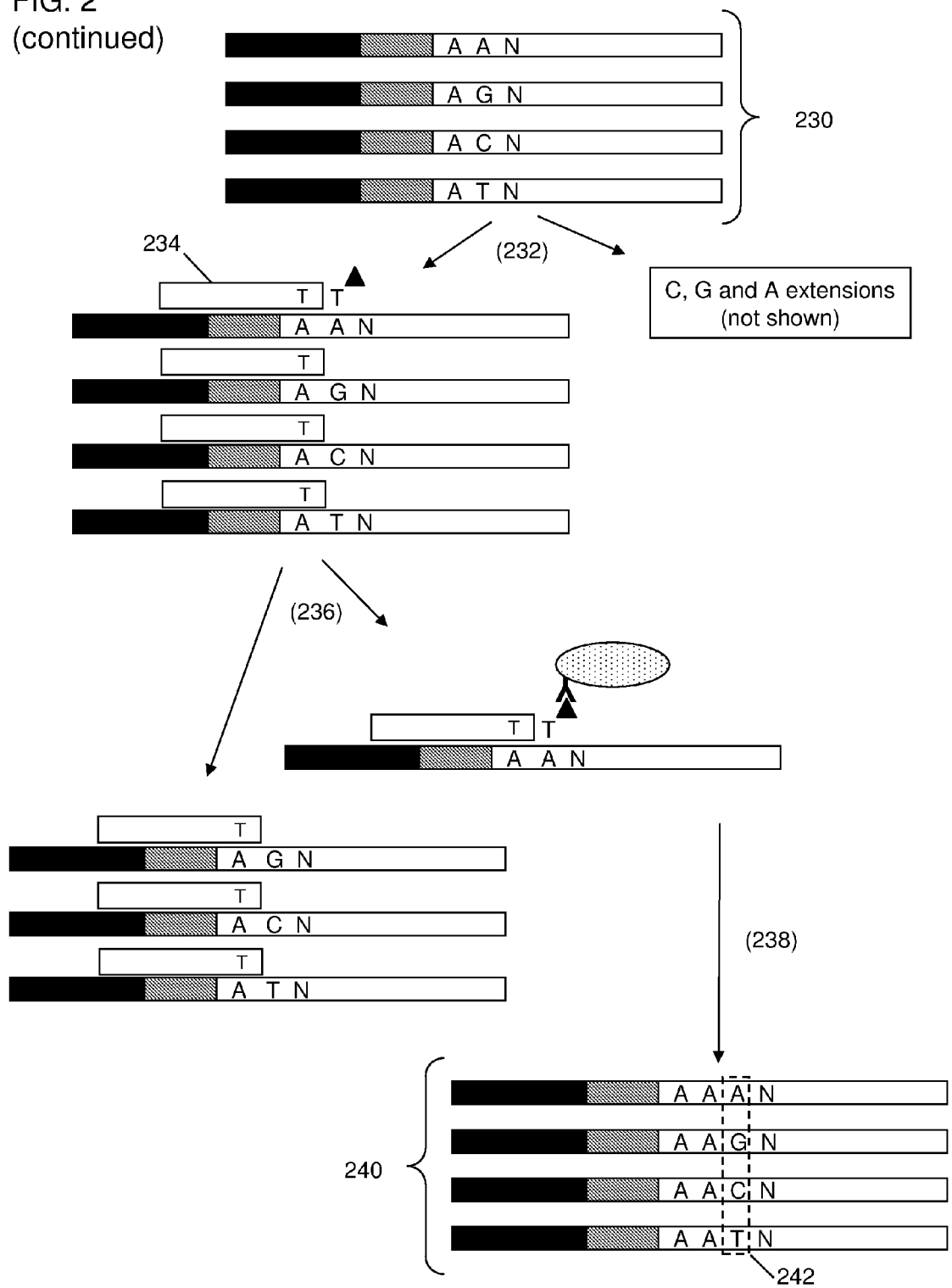

FIG. 2 provides an exemplary diagram of the above-described process starting with a population of nucleic acids (200), sometimes called a parent population, that have already been fragmented with a restriction enzyme, where the restriction enzyme recognition site is shown in grey (202), and which have an adaptor (204) ligated to one end.

It is noted here that this example does not show the use of Type IIs restriction enzymes. However, as Type IIs restriction enzymes can be used to fragment nucleic acids in the present invention (as described above), the description below should not be construed as excluding their use in the methods of the subject invention.

Ligation of adaptors can be carried out using any convenient method. For example, adaptor ligation can be performed as described in U.S. Pat. No. 6,045,994 (AFLP reactions) or U.S. provisional application 61/049,323 filed on Apr. 30, 2008 entitled "Asymmetric Adaptor Library Construction", both of which are incorporated herein by reference. The first differentiating nucleotide position of the adaptor ligated fragments is shown in dotted line box (201). The "N" nucleotides represent the second differentiating nucleotide position in each fragment, which can be any of A, G, C or T, and are not specifically shown to conserve space. In FIG. 2, the adaptor-ligated fragments are shown as a single strand in the 3'-5' orientation for ease in depicting primer binding and extension reaction in subsequent steps.

In step 206, a synthesis primer 208 (sometimes called a polymerization primer) is annealed to the fragments of population 200 and placed under nucleic acid synthesis conditions with a dTTP 210 having a capture moiety 212 (e.g., biotin) (arrow 205). As shown in FIG. 2 and described above, the synthesis primer anneals immediately upstream of the first differentiating nucleotide position of each of the fragments. Once the synthesis primer is annealed, all or a portion of the synthesis primer annealed fragments are placed under nucleic acid synthesis conditions in the presence of a differentiating nucleotide mix (sometimes referred to as a differentiating base mix). By differentiating nucleotide mix is meant a mix that allows fragments having a predetermined base at a differentiating nucleotide position to be isolated from fragments that do not. This is achieved by including in a specific differentiating nucleotide mix (i.e., one that is employed to isolate fragments having a predetermined base at a differentiating nucleotide position) one or more nucleotide bases that are differentially incorporated into synthesis-primer annealed fragments based on the identity of the nucleotide at the differentiating nucleotide position being interrogated. For example, in FIG. 2 at step 206 (arrow 205), the differentiating nucleotide mix includes a T nucleotide 210 with a capture moiety 212. This base is incorporated into fragments having an "A" present in the first differentiating nucleotide position in the template strand (i.e., the fragment). In certain embodiments, the nucleotide employed is a synthesis terminating nucleotide (e.g., a dideoxynucleotide; e.g., ddTTP). As indicated with arrow 207, the C, G and A extension reactions are not shown. The G, C, and A extension reactions may be carried out sequentially or in parallel to the T extension reaction (described in further detail below). In addition to nucleotide bases, differentiating nucleotide mixes may also contain other constituents useful for primer extension, including nucleotide polymerases, buffer components, etc. As such, the word "mix" in the term "differentiating nucleotide mix" should not be construed to mean that it must contain more than a single nucleotide base: indeed certain differentiating nucleotide mixes have a single nucleotide base (as described above). Rather, the word "mix" in this context means that a differentiating nucleotide mix can include other extension reaction components.

This step of extension may also be referred to as "template-dependent extension", which means a process of extending a primer on a template nucleic acid that produces an extension product, i.e. an oligonucleotide that comprises the primer plus one or more nucleotides that are complementary to the template nucleic acid. Template-dependent extension may be carried out several ways, including chemical ligation, enzymatic ligation, enzymatic polymerization, or the like. In certain embodiments, enzymatic extensions are employed as the requirement for enzymatic recognition increases the specificity of the reaction. In one aspect, such extension is carried out using a polymerase in conventional reaction, wherein a DNA polymerase extends primer 208 in the presence of at least one nucleotide (e.g., dNTP) labeled with a capture moiety. Depending on the embodiment, there may be from one to four nucleotides (so that synthesis proceeds at any one, a subset, or at all of the four natural nucleotides). For example, if only a single capture moiety is employed, e.g. biotin, extension may take place in four separate reactions, wherein each reaction has distinct differentiating nucleotide mix containing a different nucleotide, e.g. biotinylated deoxyadenosine triphosphate (dATP), biotinylated deoxycytidine triphosphate (dCTP), and so on. On the other hand, if four different capture moieties are employed, then four nucleotides may be used in a single reaction containing a single differentiating nucleotide mix. Any convenient capture moiety can be used, including biotin, fluorescein, dinitrophenol, digoxigenin, and the like (Perkin Elmer Lifesciences). In one aspect of the invention, four separate reactions are carried out, each reaction employing only one of the four nucleotides, biotin-dATP, biotin-dCTP, biotin-dGTP, or biotin-dTTP. In certain embodiments, in such reactions dideoxy-NTPs without capture moieties corresponding to the remaining three bases are also included in the differentiating nucleotide mix to minimize misincorporation (e.g., a reaction may include biotinylated-dTTP with ddGTP, ddCTP and ddATP).

It is noted here that a differentiating nucleotide mix can include any combination of nucleotide bases that serve to allow downstream isolation of a fragment having a base of predetermined identity at a differentiating nucleotide position being interrogated. In certain embodiments, a differentiating nucleotide mix allows isolation of fragments having one of two or three predetermined bases at a differentiating nucleotide position (e.g., a differentiating nucleotide mix can be employed that allows fragments having either A or T at a differentiating nucleotide position to be isolated). As such, a differentiating nucleotide mix can include one or more of virtually any type of nucleotide, including, but not limited to: ribonucleotides, deoxyribonucleotides, terminating nucleotides (e.g., one or more ddNTP), nucleotides having labels (e.g., capture moieties, detectible moieties, or both), nucleotides having specific chemical modifications (e.g., alpha-thio dNTPs), etc. Moreover, the sequence of the synthesis primer can also be used to interrogate a fragment at a differentiating nucleotide position. For example, a synthesis primer may include an additional base at its 3' end that is complementary to only one specific base at the differentiating nucleotide position being interrogated. Using such a synthesis primer allows the addition of a base at successive differentiating nucleotide positions only if the fragment has a base that is complementary to the base at the 3' end of the synthesis primer. In addition, a synthesis primer may include bases having distinct characteristics (as compared to standard ribo- or deoxyrbo nucleotide bases). For example, a synthesis primer can include an alpha-thio nucleotide base at its 3' end, the presence of which increases the stringency of nucleotide addition at the subsequent position. As another example, a synthesis primer may contain a nucleotide base that can base pair with more than one nucleotide (e.g., inosine) (see, e.g., J.

Zhang et al, Journal of Biochemistry and Molecular Biology, 2003 volume 36(6), pp 529-532). As is clear from this brief description, there exist an extraordinary number of combinations of differentiating nucleotide mixes and synthesis primers that can be employed in producing reduced complexity samples according to aspects of the present invention.

As illustrated in step 214, primers extended to incorporate a T with a capture moiety are captured with a capture agent 216 on a solid support 218, e.g., a substrate. The substrate can be any of a variety of substrates known in the art for immobilization (e.g., magnetic particle, Sepharose™, agarose, silicone, nitrocellulose, etc.) so long as it does not interfere with the reactions of the assay (e.g., nucleic acid polymerization). The substrate may take any convenient form, including but not limited to beads, pins, membranes, columns, etc. Captured polynucleotides are separated and eluted from the extended primers (e.g., by melting, denaturation, etc.) in step 220 to form population 230 that has a lower complexity than that of the parent population 200. Population 230 is now shown as having an A at the first differentiating nucleotide position (i.e., the position that has been sorted for having an A at that site) followed by one of four bases at the second differentiating nucleotide position 231 and any nucleotide "N" at the third differentiating nucleotide position. As indicated above, any convenient capture agents can be employed, including, but not limited to, avidin, streptavidin, and antibodies, especially monoclonal antibodies, that form specific and strong complexes with capture moieties. Many such antibodies are commercially available that specifically bind to biotin, fluorescein, dinitrophenol, digoxigenin, rhodamine, and the like (e.g. Molecular Probes, Eugene, Oreg.).

As noted above, successive rounds of selection can be carried out using a set of overlapping primers to separate a population of nucleic acid fragments into subsets of polynucleotides having a common, specific sequence of nucleotides in successive differentiating nucleotide positions (e.g., a sequence adjacent to a restriction enzyme site). As shown in step 232 of FIG. 2, synthesis primers 234 is annealed to previously sorted population 230 (i.e., having an A at the first differentiation position), where primer 234 is identical to previously employed primer 208 except that it includes an additional "T" at the 3' end. A "T" is used for population 230 because it is known that these fragments have an "A" at the first differentiating nucleotide position as a result of the previous sorting steps. In other words, the primer is selected so that when it anneals it base-pairs one base downstream relative to the binding site of the previous primer. This primer is thus "indexed" based on the previous sorting process. Correspondingly indexed primers can be used for sorted fragment populations having a "G", "C" or "T" at the first differentiating nucleotide position (not shown). Steps 236 and 238 of FIG. 2 correspond to previous steps 214 and 220. These steps result in a population of fragments 240 in which the identity of the nucleotides at the first and second differentiating nucleotide positions are "A" and the nucleotide at the third differentiating nucleotide position 242 is one of four nucleotides.

Further successive cycles of annealing primers, extension, capture, and eluting may be carried out with a set of primers that permits the sorting of a parent population of polynucleotides into subpopulations that each have the same sequence at a region adjacent to the restriction site.

Another exemplary sorting process according to the present invention is shown in FIG. 3. In the embodiments shown in FIG. 3, the population of fragments is sorted based on the identity of the nucleotide at the differentiating nucleotide position (or positions), but the specific steps employed to achieve this result are distinct from those shown in FIG. 2.

In FIG. 3, a genomic DNA sample 300 has been fragmented and has been ligated with distinct oligonucleotides at either end: an "X" adaptor tag 302 on one end and a "Y" adaptor tag 304 on the other, where the "Y" adaptor tag includes a region having a sequence different from the "X" adaptor tag. In the embodiment shown, the X tag 302 includes a 5' capture moiety 312. In step 320, the sample is melted, the upper strand is removed by contacting the sample with a binding partner for the capture moiety immobilized on a substrate (not shown), and the remaining (lower) strand is immobilized to substrate 330 by hybridizing it to an oligonucleotide 332 that is complementary to all or a portion of the different region in the Y adaptor tag. Also in step 320, a synthesis primer 334 that hybridizes immediately upstream of the first differentiating nucleotide position 330 is annealed (e.g., as is described above for FIGS. 1 and 2). As shown in FIGS. 2 and 3, synthesis primers may not be complementary to the entire adaptor region (e.g., the 5' end of the synthesis primers shown do not extend to the 3' end of the adaptor sequence in the template strand), although in certain embodiments this can be the case. Moreover, the "Y" tag can include sequences other than the region employed for immobilization to the substrate. It is noted here that the restriction enzyme recognition site that was used to fragment the sample is not shown as it was in FIG. 2. In the embodiments shown in FIG. 3, the synthesis primer 334 includes a capture moiety 312 that serves to facilitate upper strand removal in subsequent rounds of sorting.

In step 340, the immobilized fragments are placed under nucleic acid synthesis conditions in a differentiating nucleotide mix in which terminating nucleotide bases are present that are complementary to the all of the bases except a predetermined base (i.e., terminating nucleotide bases are present for nucleotides not being sorted for in this step). In FIG. 3, the predetermined nucleotide at the differentiating nucleotide position being sorted for is A in the template strand (342), and as such, the terminating nucleotides ddCTP, ddGTP and ddATP have been included in the differentiating nucleotide mix used for this polymerization step. This results in the incorporation of a strand-terminating base in all fragments that do not have an A at the first differentiating nucleotide position. Strand terminating bases are indicated by C* 344, G* 346 and A* 348.

After completion of the terminating base incorporation, the terminating bases are removed (e.g., the immobilized fragments are subjected to a wash step) and the immobilized fragments are placed under nucleic acid synthesis conditions with all four nucleotide bases and a strand-displacing polymerase (e.g., Klenow). Because only fragments having an A at the first differentiating nucleotide position can support nucleic acid synthesis, only these strands will be extended at this stage (denoted by dotted arrow 350). Because a strand displacing polymerase is employed, completion of this synthesis reaction will elute all fragments having an A at the first differentiating nucleotide position from the immobilizing oligo (indicated at 352) resulting in sorted population 360. Fragments in which strand synthesis was terminated (population 370) will remain immobilized to the substrate (via continued interaction with the immobilization oligo) and be removed from the sample. The sorted population 360 can then be sorted based on the identity of the next differentiating nucleotide position using synthesis primers indexed to the next differentiating nucleotide position (as described above).

In certain embodiments of the present invention, the number of synthesis primers needed to implement multiple rounds of sorting as described above could be calculated as: $1+4+4^2 \ldots +4^{n-1}$ (where n is the number of rounds of sorting performed; assuming more than 3 rounds in this case). The basis for this calculation is that each successive round of sorting leads to a 4-fold increase in the number of binned fragment samples (i.e., every starting sample is sorted into 4 distinct binned samples at each step). Because the fragments in each successive binned sample (after the starting parent sample) has a unique base or sequence of bases to which the 3' end of the synthesis primer must be complementary, a different synthesis primer is needed for each. Using this calculation, sorting a parent sample for all four bases at the first 5 differentiating nucleotide positions would require 341 separate synthesis primers (i.e., 1+4+16+64+256=341).

In certain embodiments, the number of synthesis primers employed may be reduced from this baseline amount. For example, one could design synthesis primers that can be employed in multiple binned samples by incorporating bases that do not have base discrimination at certain locations (i.e., bases that can base-pair with more than one base, e.g., inosine, 8-oxopurine, and the like).

In certain embodiments, after each cycle (or after a specified number of cycles) the selected polynucleotides are amplified to increase the quantity of material for subsequent sorting reactions. In certain embodiments, the selected polynucleotides are amplified using polymerase chain reaction (PCR), e.g., using primer pairs that anneal to adaptors ligated to the ends of each fragment. In one aspect, amplification is carried out by a conventional linear amplification reaction using a primer that binds to one of the flanking adaptors and a high fidelity DNA polymerase. In certain other embodiments, an adaptor ligated to the fragments can include an in vitro transcription promoter (e.g., T3 or T7) which can be employed to amplify the nucleic acids in the sample by an RNA polymerase. In certain embodiments, the same number of amplification cycles is carried out in each sorted sample for each round of sorting, whereas in other embodiments, amplification is performed at only one step, or a subset of steps, in the sorting process. As such, the implementation of an amplification step or steps can vary widely.

Virtually any population of polynucleotides may be sorted into reduced complexity samples according to the presently described invention. In certain embodiments, the population of polynucleotides sorted is a genomic polynucleotide sample, where genomic polynucleotides from one or more subjects/sources are present in the sample. In certain embodiments, populations of polynucleotides sorted are genomic polynucleotides of organism(s) whose sequences are not known, whereas in certain other embodiments, populations of polynucleotides sorted are genomic polynucleotides of organism(s) whose sequences are known. The genomes may be from any organism, including plant, animal, bacteria, or the like. When genomic DNA is obtained for medical or diagnostic use, it may be obtained from a wide variety of sources, including tissue biopsies, blood samples, amniotic cells, and the like. Genomic DNA is extracted from such tissues by conventional techniques, e.g. as disclosed in Berger and Kimmel, Editors, Methods in Enzymology, Vol. 152, Guide to Molecular Cloning Techniques (Academic Press, New York, 1987), or the like.

Polynucleotides in a polynucleotide sample being analyzed (or processed) in accordance with the present invention can be from any polynucleotide source, including but not limited to genomic DNA, complementary DNA (cDNA), RNA (e.g., messenger RNA, ribosomal RNA, short interfering RNA, microRNA, etc.), plasmid DNA, mitochondrial DNA, etc. Furthermore, as any organism can be used as a source of nucleic acids to be processed in accordance with the present invention, no limitation in that regard is intended. Exemplary organisms include, but are not limited to, plants, animals (e.g., reptiles, mammals, insects, worms, fish, etc.), bacteria, fungi (e.g., yeast), viruses, etc. In certain embodiments, the nucleic acids in the nucleic acid sample are derived from a mammal, where in certain embodiments the mammal is a human.

In certain embodiments, nucleic acids in the nucleic acid sample are amplified prior to analysis. Any convenient method for performing amplification reactions on a starting nucleic acid sample can be used in practicing the subject invention. In certain embodiments, the nucleic acid polymerase employed in the amplification reaction is a polymerase that has proofreading capability (e.g., phi29 DNA Polymerase, *Thermococcus litoralis* DNA polymerase, *Pyrococcus furiosus* DNA polymerase, etc.).

In certain embodiments, the nucleic acid sample being analyzed is derived from a single source (e.g., a single organism, tissue, cell, subject, etc.), whereas in other embodiments, the nucleic acid sample is a pool of nucleic acids extracted from a plurality of sources (e.g., a pool of nucleic acids from a plurality of organisms, tissues, cells, subjects, etc.), where by "plurality" is meant two or more. As such, in certain embodiments, a nucleic acid sample can contain nucleic acids from 2 or more sources, 3 or more sources, 5 or more sources, 10 or more sources, 50 or more sources, 100 or more sources, 500 or more sources, 1000 or more sources, 5000 or more sources, up to and including about 10,000 or more sources. As described above, the nucleic acids in nucleic acid samples from a single source as well as from multiple sources include a locus of interest for which at least one reference sequence is known.

In embodiments where a pooled nucleic acid sample is processed, the nucleic acids derived from each of the sources may be uniquely tagged with an identity tag. In certain embodiments, an identity tag may be included as part of an attached adapter (e.g., as part of the sequence of a ligated adaptor that also contains sequences that hybridize to the synthesis primer(s)), whereas in other embodiments, an identity tag may be ligated independently to the fragments on a sample (e.g., prior to mixing the multiple fragmented nucleic acid samples). In these embodiments, the source from which the sorted polynucleotide fragments were derived can be determined by decoding the identity tag on the fragment (e.g., by sequencing, hybridizing to specific oligonucleotides complementary to the an identity tag, etc.). In general, tagging of a nucleic acid sample will occur after fragmentation of the nucleic acids in the sample (e.g., by restriction enzyme digest). Any convenient method for uniquely tagging nucleic acids with an identity tag from multiple sources may be employed, including but not limited to those described in co-pending U.S. patent application Ser. No. 11/656,746, filed on Jan. 22, 2007, and titled "Nucleic Acid Analysis Using Sequence Tokens", co-pending U.S. patent application Ser. No. 11/377,462, filed on Mar. 16, 2006, and titled "Methods and compositions for assay readouts on multiple analytical platforms", and U.S. provisional application 61/049,323 filed on Apr. 30, 2008 entitled "Asymmetric Adaptor Library Construction", each of which are incorporated herein by reference in their entirety for their description of nucleic acid tagging and decoding.

In certain embodiments, the nucleic acids being sorted are rendered single stranded prior to analysis. Rendering nucleic acids single-stranded may be done using any convenient method, which may include, but is not limited to, amplifying the nucleic acid strand of interest using an asymmetric PCR or linear amplification reaction, strand specific immobilization, melting using temperature or denaturants, selectively digesting one strand of a duplex strand, etc. One embodiment of this latter example includes differentially marking one strand of a duplex with a specific base (e.g., placing an alpha-thio nucleotide at the 5' terminus) followed by contact with an exonuclease selective for the non-modified strand (e.g., an exonuclease blocked by the presence of a 5' alpha-thio nucleotide at the 5'end). Any convenient nucleic acid duplex modification/enzymatic digestion strategy that results in selective destruction of one strand of the duplex may be employed.

In certain embodiments, double-stranded nucleic acids of the sample being analyzed are rendered asymmetric to facilitate the isolation and/or amplification of a single-stranded template for processing. Any convenient method for rendering a double-stranded nucleic acid asymmetric may be used. For example, U.S. patent application Ser. No. 12/163,571 entitled "Methods and compositions for isolating nucleic acid sequence variants" filed on Jun. 27, 2008, describes one method for rendering nucleic acids asymmetric, the entirety of which is incorporated herein by reference. This method is but one exemplary method that can be used to create asymmetric DNA of one strand. Other methods known in the art may be used to produce asymmetric DNA, e.g., asymmetric PCR.

Utility

As noted above, the production of reduced-complexity samples according to the present invention finds use in a wide variety of downstream genetic analyses/manipulations, including those based on sequence-specific hybridization (e.g., array assays, comparative genomic hybridization assays (CGH), pull-out/extraction assays using oligonucleotide probes, amplification reactions (e.g., PCR), etc.), sequencing-based analysis (e.g., high throughput sequencing) and fragment analysis (e.g., based on size or other physical properties).

Figure 4:
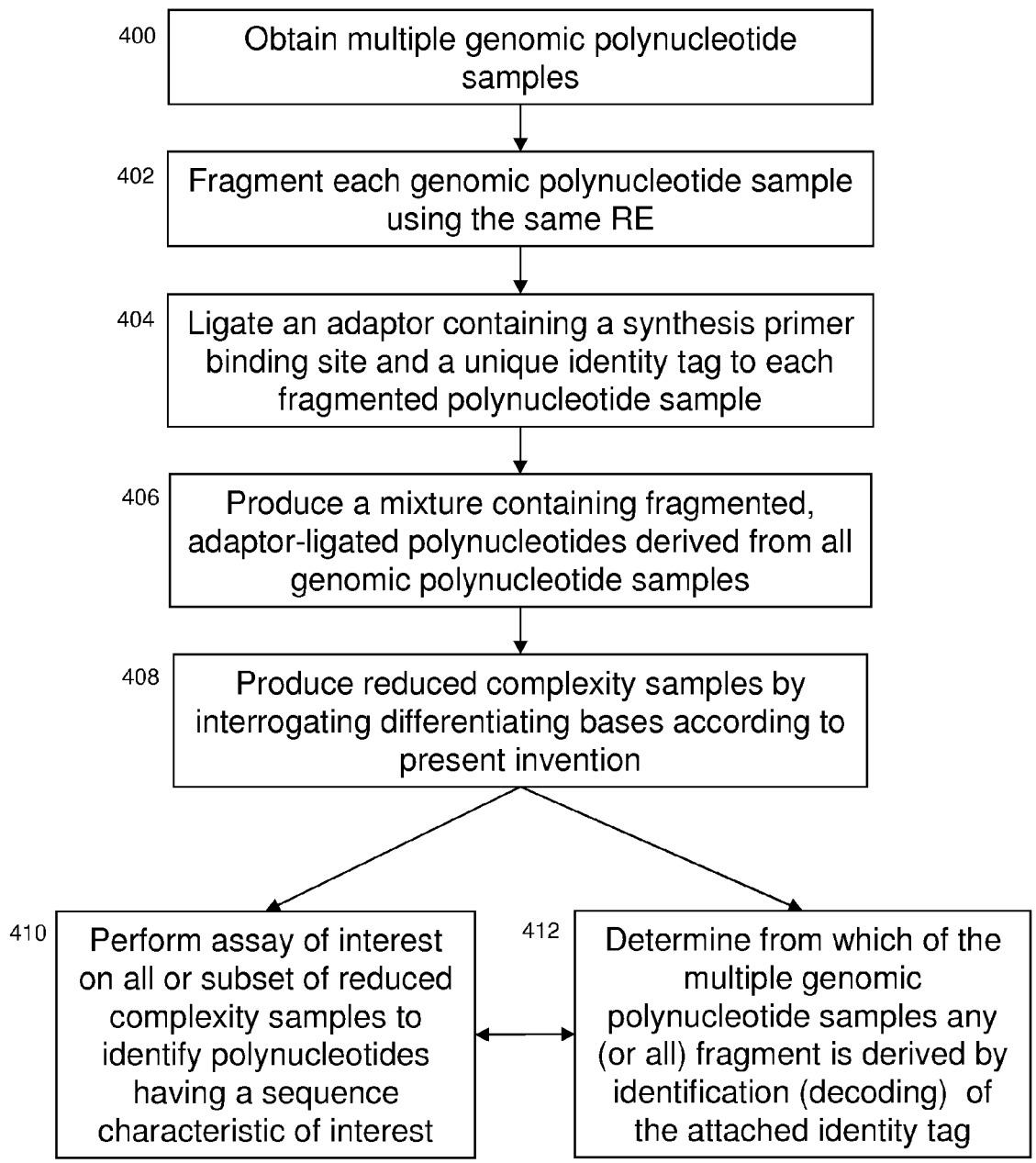
FIG. 4 provides a flowchart of an exemplary assay that includes complexity reduction according to the present invention and downstream analysis.

FIG. 4 provides a basic flowchart depicting an embodiment of how the complexity reducing methods and compositions of the present invention can be integrated into genomic analyses. At step 400, a set of genomic samples of interest is obtained. At step 402, each of the genomic samples is digested with the same restriction enzyme followed by ligating an adaptor containing a synthesis primer binding site and a unique identity tag to each fragmented polynucleotide sample at step 404. The adaptor ligated fragments from the genomic samples are then mixed at step 406 and at step 408 the mixed sample is subjected to complexity reduction as described herein (to produce one or a set of samples having reduced complexity). Once such a reduced complexity sample(s) is formed, any number of different analyses can be performed, as depicted in 410 and 412. In its simplest form, the fragments in a reduced complexity sample(s) can be assayed for the presence of a sequence characteristic of interest. For example, a specific reduced complexity sample can be assayed to determine if it contains any fragments having a particular (or any) polymorphism (e.g., by sequencing the fragments, by fragment pull-out assays, etc.). This is possible due to the fact that all of the fragments in the mixed genomic sample were subjected to the same complexity reduction process which means that each of the reduced complexity samples will contain the same corresponding fragments from their respective parent samples (and if the genomic sequence is known beforehand, one can predict in which reduced complexity sample a particular fragment resides). In addition to determining a sequence characteristic of one or more fragments in a reduced complexity sample, the original sample from which all or a subset of fragments in the sample were derived can be determined by decoding their respective identity tags, e.g., by sequencing or a suitably designed hybridization assay (step 412). In certain embodiments, both decoding of the identity and determination of a sequence characteristic for one or more fragments in a reduced complexity sample are determined (depicted by arrow 414). For example, fragments in a reduced complexity sample may be fully sequenced to provide sequence information for both the fragment and identity tag.

Exemplary uses of reduced complexity samples are described below, which are in no way meant to be limiting with regard to the utility of the present invention. As noted in the Definitions section above, a reduced complexity sample according to the subject invention that has been altered (e.g., chemically, enzymatically, physically, etc.), processed or analyzed further is sometimes referred to as a "modified" sample. If and to what extent a reduced complexity sample is "modified" will depend on the desires of the user of the subject methods or, in certain embodiments, a secondary user who obtains a reduced complexity sample from a primary user (e.g., as may occur in a vendor/customer relationship or between two collaborating entities).

The sorting methods and compositions of the present invention find use in reducing the complexity of samples prior to sequencing. Complexity-reduced samples are of particular value for use in new sequencing approaches that simultaneously analyze all of the fragments present in a sample, such as massively parallel pyro-sequencing (e.g., 454® sequencing (Roche Applied Science)), SOLID™ system sequencing (Applied Biosystems, Inc.), Genome Analyzer system sequencing (Illumina), etc. The process of sequencing is inherently much more efficient if the system is presented only with the subset or subsets of the genome which are relevant to a particular analysis or experiment.

For example, consider an embodiment in which the same adaptor is ligated to both ends of each fragment of a fragmented sample followed by performing 5 rounds of sorting according to certain embodiments of the present invention. This will generate 1024 samples with a complexity that is 512-fold less complex than the starting population (the complexity is only 512-fold less than the parent because a specific fragment will be sorted into a first sample based on the identity of the sequence of the differentiating nucleotide positions interrogated at the first end as well as a second sample based on the identity of the sequence of the differentiating nucleotide positions interrogated at the second end). This is equivalent to reducing the complexity of a human genomic nucleic acid sample into 1024 samples each having a complexity approximating that of a bacterial genome. Further, when sorting nucleic acid samples having a known sequence (e.g., a human genome), the choice of which sorted sample to analyze can be determined by virtue of the identity of the nucleotides at the differentiating nucleotide positions in each sorted sample. In other words, if a particular genomic locus is to be analyzed, one can predict in which sorted well it is located based on the identity of the nucleotides at the differentiating nucleotide positions that have been analyzed. It is again noted that in certain embodiments, fragments comprising a particular genomic locus may be predicted to be present in two distinct sorted wells (or bins) based on the identity of the nucleotide(s) at the differentiating nucleotide position(s) at each end of the fragment (which can be different from one another). Given the ever expanding amount of sequence information, it is easy to envision bioinformatic methods designed to direct the user to a specific well (or wells) that contain a fragments having a region/locus of interest.

The sorting methods and compositions of the present invention find use in reducing the complexity of samples prior to performing genomic assays based on sequence-specific hybridization. For example, the complexity-reduction methods and compositions described herein facilitate assays in which certain genomic regions are "pulled out" (or extracted, or isolated) from a sample based on the hybridization of an oligonucleotide to a particular sequence, in some cases employing additional enzymatic manipulation (see, e.g., U.S. Pat. No. 7,217,522 entitled "Genetic Analysis by Sequence Specific Sorting" by Brenner et al., incorporated herein by reference for its description of pull out/extraction assays). This is because the complexity of the pool from which the pull-out is occurring is much less complex, and thus will be accomplished with much higher efficiency and specificity.

As another example, the complexity-reduction methods and compositions described herein facilitate assays in which the differences between genomes/genomic fragments are directly identified using methods based on co-hybridization between genomes.

For example, U.S. patent application Ser. No. 11/656,746, filed on Jan. 22, 2007, describes co-hybridization based methods for detecting one or more polymorphism in a nucleic acid sample (e.g., a genomic sample) of interest using wild-type RNA probes (U.S. patent application Ser. No. 11/656,746 is incorporated herein by reference for its description of such polymorphism-detection assays). Briefly, single stranded RNA probes of the nucleic acid region of interest lacking the polymorphism are combined with the reduced complexity DNA fragments (i.e., a reduced complexity sample containing fragments that include the region of interest) and the mixture is allowed to denature and anneal to form heteroduplexes of RNA and DNA. Any double stranded heteroduplex molecules in the composition having a DNA strand that includes the polymorphism and a RNA strand lacking the polymorphism will result in a mismatch at the polymorphism. The heteroduplex molecules are then treated with RNAse I to nick the RNA molecules at the mismatch, remove the mismatch nucleotide, and produce a 3' phosphate on the nicked RNA strand. The 3' phosphate can then be removed using alkaline phosphatase and using a polymerase (e.g., T7), a capture moiety-labeled-NTP is incorporated at the site of the nick (capture moieties are described above). The capture moiety can then be used to separate nucleic acids having the polymorphism from nucleic acids that do not. Once captured/isolated, such fragments may be further processed to positively identify the polymorphism present in the fragment as well as to identify from which original subject/sample the polymorphism-containing fragment was derived by decoding the identity tag.

Another way to perform such assays is to label the genomes/genomic fragments being compared, combine them in a sample, denature and anneal them to form hybrid double stranded polynucleotides. If perfectly matched double helices are formed, then the genomes are identical. However, any imperfect duplexes (i.e., those with mismatched bases) indicate the present of a difference between the two genomes/genomic fragments (e.g., a mutation, polymorphism, etc.). Such matches can be identified and specifically "pulled out" from the sample, for example as described above or based on other enzymatic, chemical or biophysical discrimination, such as mismatch cleavage, separation by mobility differences, etc. These types of assays can be achieved with small genomes and with fragments of large genomes (e.g., on arrays), but is not practical with large complex genomes (e.g., human genomes) due to the kinetics of hybridization.

The fundamental equation describing the rate of formation of double-stranded DNA is as follows:

$$c/c_o = (1+kc_ot)^{-1}$$

where $c_o$ is the initial concentration in moles nucleotide per liter, c is the concentration of annealed molecules formed by time t (in seconds), and k is the rate constant. The half-time of annealing is when $c/c_o$ is ½, at which time the equation becomes:

$$½=(1+kc_ot_{1/2})^{-1}$$

or $$kc_ot_{1/2}=1$$

or $$c_ot_{1/2}=1/k.$$

Rate constant k varies with the length of the DNA and has been determined to be 0.22 milliseconds for the 4.64×10⁶ basepair (bp) genome of E. coli; $c_ot_{1/2}$ for E. coli is therefore 1/0.022=4.54 mole/liter seconds [see, e.g., Daniel G. Peterson et al., Genome Research, 12 pp 795-807 (2002); and A. Kornberg and T. Baker, DNA Replication, W.H. Freeman and Co., New York, pages 14-15 (1992)]. Thus, at 300 μg/ml (or 10⁻³M), $c_ot_{1/2}$ will be reached in 4540 seconds=75 minutes, or 1.25 hours. We can now calculate $c_ot_{1/2}$ for the human genome with estimated unique sequence length of about 2×10⁹ base pairs. As compared to the E. coli example, $c_ot_{1/2}$ will be increased by (2/4.64)×10³, which equals 4.3×10². Thus, at the same concentration, it will take human DNA 538 hours, or 22.5 days, to anneal to 50%. We also know that 85% of the DNA will be annealed at ten times the half-time of annealing. For the human genome, this translates into 30 weeks (or more than 6 months). For the E. coli genome, this translates into only about 12.5 hours, or ½ day.

It can be readily seen that one cannot anneal complex genomes together, e.g., like the human genome, in practical amounts of time. In addition, when sheared DNA is used, the repetitive sequences anneal rapidly and add further complications. Therefore, employing reduced complexity samples of large genomes as described herein provides a way to dramatically reduce annealing times for whole genomes (e.g., by performing annealing reactions in parallel using corresponding reduced complexity samples representing the entire genome of each genome of interest and then processing such annealed samples so as to separate those mismatched fragments, and their identity tags, as appropriate, from perfectly matched fragments). This makes direct genome comparison utilizing co-hybridization techniques easily possible. Indeed, if not for complexity reduction it would not be practical to compare complex genomes using co-hybridization methodologies.

As described above, in certain embodiments the initial sample of interest is a mixture of nucleic acids derived from distinct subjects (or tissues) that are each uniquely tagged. In such embodiments, the reduced complexity samples (or fragments extracted from a reduced complexity sample) can be analyzed for the identity of the using sequencing methods that have the capacity to sequence a long portion of, if not the entire fragment (e.g., 454® sequencing; see, e.g., Marguiles et al., "Genome sequencing in microfabricated high-density picolitre reactors" Nature. Sep. 15, 2005;437(7057):376-80). Sequencing a sufficiently long portion of the entire length of the fragments enables one to link the sequence of the fragment to the identity of its source, thus greatly facilitating variant analysis of loci of interest (i.e., loci present in the fragments in the reduced complexity sample) at the population level.

As reviewed above, the complexity reducing methods and compositions of the present invention find use in combination with any number of other genetic analysis methods that would benefit from having a reduced complexity starting material, including comparative genome hybridization (CGH), rare allele detection (e.g., heteroduplex mismatch strategies, primer extension and retrieval strategies, etc.), mutation analyses, and the like. Examples of such downstream assays include those described in the following references, all of which are incorporated herein by references: Okuo et al., Nature Methods "Microarray based genomic selection for high throughput resequencing", published online on Oct. 14, 2007; Albert et al., Nature Methods "Direct selection of human genomic loci by microarray hybridization", published online on Oct. 14, 2007; and US Patent Publication Number 20060046251. It is again noted here that, unlike the extraction/enrichment methods described in these references, the complexity reduction described in the present application is applicable to any complex sample of polynucleotides as it does not rely on targeting specific loci in the genome to produce selected samples (e.g., employing an array of locus-specific probes to capture polynucleotides via sequence-specific hybridization). Indeed, the production of reduced complexity samples as described herein can be applied to complex polynucleotide samples for which little or no sequence information is known. However, in embodiments in which sequencing information is available for the polynucleotides in the complex sample of interest, the location of particular fragments can be deduced (as noted above).

In certain embodiments, two or more reduced complexity samples produced by the methods of the present invention are re-combined for further genetic analysis. For example, a user may wish to analyze a specific subset of reduced complexity samples by sequence analysis (e.g., high throughput sequencing) based upon the specific subset of fragments known to be present in each (e.g., they both may have fragments containing genes related to one another, e.g., known to be mutated in a specific disease). As another example, a user may perform a "pull-out" assay on some or all of the reduced complexity samples (e.g., to isolate fragments having one or more polymorphism or other sequence characteristic of interest) and combine these pulled-out fragments to process further (e.g., to sequence them to identify the polymorphism/sequence characteristic and/or the fragment's origin, e.g., through analysis of the sequence of the identity tag). As yet another example, a user may perform the hybridization step of a "pull-out" assay on, or in some other way create modified versions of, some or all of the reduced complexity samples (e.g., hybridization between two genomes, as described above) and once the hybridization step is completed, combine the samples prior to performing the "pull-out" step and doing the subsequent sequencing.

As is readily apparent, there are myriad ways to utilize the reduced complexity samples described herein to facilitate nucleic acid analysis. As such, the description of exemplary uses of reduced complexity samples detailed above is in no way meant to be limiting.

Kits and Systems

Also provided by the subject invention are kits and systems for practicing the subject methods, as described above. In some embodiments, systems and kits contain programming means to allow a robotic system to perform the subject methods, e.g., programming for instructing a robotic pipettor to add, mix and remove reagents in accordance with one or more complexity reducing sorting operations, as described above. Systems may include robotic components for carrying out one or more of the steps of the subject methods and be configured for use with the subject kits (described below). The various components of the kits may be present in separate containers or certain compatible components may be precombined into a single container, as desired.

The subject systems and kits may also include one or more other reagents for preparing or processing a sample according to the subject methods (e.g., restriction enzymes, adaptors, synthesis reagent sets, unique tagging reagents, sets of synthesis oligonucleotides, displacement synthesis reagents, solid immobilization surfaces, e.g., combs, pins, etc.). The reagents may include one or more matrices, solvents, sample preparation reagents, buffers, desalting reagents, enzymatic reagents, denaturing reagents, where calibration standards such as positive and negative controls may be provided as well. As such, the kits may include one or more containers such as vials or bottles, with each container containing a separate component for carrying out a sample processing or preparing step and/or for carrying out one or more steps of a nucleic acid variant isolation assay according to the present invention.

In addition to above-mentioned components, the subject kits typically further include instructions for using the components of the kit to practice the subject methods, e.g., to produce reduced complexity samples according to the methods of the subject invention. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and That which is claimed is:

1. A method of producing one or more polynucleotide samples having reduced complexity from a parent polynucleotide sample, said method comprising:
   (i) fragmenting polynucleotides in a parent polynucleotide sample;
   (ii) ligating a first oligonucleotide adapter to said polynucleotide fragments;
   (iii) annealing a first nucleic acid synthesis primer to said oligonucleotide adapter-ligated fragments, wherein said nucleic acid synthesis primer anneals such that its 3' base is immediately upstream of a first differentiating nucleotide position in each fragment;
   (iv) contacting said synthesis-primer annealed fragments with a differentiating nucleotide mix under nucleic acid synthesis conditions, wherein said differentiating nucleotide mix comprises one or more nucleotide that is differentially incorporated into said synthesis-primer annealed fragments according to the identity of the nucleotide at said first differentiating nucleotide position; and
   (v) isolating polynucleotide fragments having a nucleotide of predetermined identity at said first differentiating nucleotide position, wherein said fragments are isolated based on the differential incorporation of said one or more nucleotide, thereby producing one or more polynucleotide samples having reduced complexity from said parent.

2. The method of claim 1, wherein said parent polynucleotide sample comprises a mixture of polynucleotides from a plurality of subjects.

3. The method of claim 2, wherein said polynucleotides from said plurality of subjects are each tagged with a unique identity tag.

4. The method of claim 3, wherein said unique identity tag is present in said first oligonucleotide adapter.

5. The method of claim 1, wherein said differentiating nucleotide mix comprises a nucleotide labeled with a first member of a binding pair.

6. The method of claim 5, wherein said first member of said binding pair is biotin.

7. The method of claim 6, wherein said isolating step comprises contacting said sample to a second member of said binding pair immobilized on a substrate, removing unbound polynucleotide fragments and eluting bound fragments from said synthesis primer.

8. The method of claim 1, wherein steps (iii) to (v) are repeated one or more times at a successive differentiating nucleotide position.

9. The method of claim 1, wherein step (iv) further comprises separating said synthesis primer-annealed sample into two or more distinct wells, each of which contains a distinct differentiating nucleotide mix and whereby in step (v) multiple distinct isolated samples having reduced complexity from said parent sample are produced, wherein said nucleotide of predetermined identity at said first differentiating nucleotide position is different between said multiple distinct isolated samples.

10. The method of claim 1, wherein the sequence of the polynucleotides in said parent polynucleotide sample is known, wherein said one or more polynucleotide samples of reduced complexity comprises a predetermined set of nucleic acid fragments based on: (i) said known polynucleotide sequence, and (ii) the identity of the base at said first differentiating nucleotide position.

11. The method of claim 10, wherein steps (iii) to (v) are repeated one or more times at a successive differentiating nucleotide position, thereby producing multiple polynucleotide samples having reduced complexity from said parent polynucleotide sample, and wherein said multiple polynucleotide samples each comprise a predetermined set of polynucleotide fragments based on said known polynucleotide sequence and the identity of the bases in each of said differentiating nucleotide positions.

12. The method of claim 10, wherein a first of said one or more polynucleotide samples of reduced complexity is selected for further processing based on the identity of the predetermined set of nucleic acid fragments therein.

13. The method of claim 10, wherein said method further comprises:
   selecting two or more of said polynucleotide samples of reduced complexity;
   modifying each of said selected samples;
   combining said modified samples; and
   subjecting said combined sample to further processing.

14. The method of claim 1, wherein:
   step (ii) further comprises ligating a second oligonucleotide adapter to said polynucleotide fragments, wherein said first oligonucleotide adapter and said second oligonucleotide adapter are ligated to opposite ends of said polynucleotide fragments and said second oligonucleotide adapter comprises a region differing in sequence from said first oligonucleotide adapter;
   step (iv) further comprises immobilizing said nucleic acid fragments by hybridization to a capture primer immobilized on a substrate, wherein said capture primer hybridizes to said region in said second oligonucleotide adapter on the same strand of said nucleic acid fragments as said synthesis primer at a location that is downstream of said synthesis primer;
   said differentiating nucleotide mix comprises nucleic acid synthesis terminating nucleotides representing all nucleotides except a predetermined nucleotide; and
   step (v) further comprises removing said nucleic acid synthesis-terminating nucleotide mix from said immobilized fragments and isolating polynucleotide fragments that have said predetermined nucleotide by contacting said immobilized synthesis-primer annealed fragments with a strand-displacing nucleic acid polymerase under nucleic acid synthesis conditions in the presence of all four nucleotide bases such that fragments that have said predetermined nucleotide at said first differentiating nucleotide position are eluted from said immobilization primer by virtue of the strand-displacing activity of said strand-displacing polymerase.

15. The method of claim 14, wherein said synthesis primer comprises a capture moiety.

16. The method of claim 14, wherein the sequence of the polynucleotides in said parent polynucleotide sample is known, wherein said polynucleotide sample of reduced complexity comprises a predetermined set of nucleic acid fragments based on: (i) said known polynucleotide sequence, and (ii) the identity of the base at said first differentiating nucleotide position.

17. The method of claim 16, wherein steps (iii) to (v) are repeated one or more times at a successive differentiating nucleotide position, thereby producing multiple polynucleotide samples having reduced complexity from said parent polynucleotide sample, and wherein said resulting polynucleotide samples each comprise a predetermined set of polynucleotide fragments based on said known polynucleotide sequence and the identity of the bases in each of said differentiating nucleotide positions.

18. A method comprising:
   obtaining a polynucleotide sample having reduced complexity from a parent polynucleotide sample produced by the method of claim 1.

19. The method of claim 18, wherein said polynucleotide sample having reduced complexity is modified prior to said obtaining.

* * * * *